(12) United States Patent
Chopra et al.

(10) Patent No.: US 8,765,978 B2
(45) Date of Patent: Jul. 1, 2014

(54) METHOD OF MAKING INDENO-FUSED NAPHTHOL MATERIALS

(75) Inventors: Anu Chopra, Pittsburgh, PA (US); Barry Van Gemert, Delmont, PA (US); Wenjing Xiao, Murrysville, PA (US); Huayun Yu, Monroeville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 13/324,345

(22) Filed: Dec. 13, 2011

(65) Prior Publication Data

US 2012/0157696 A1 Jun. 21, 2012

Related U.S. Application Data

(60) Provisional application No. 61/459,617, filed on Dec. 16, 2010.

(51) Int. Cl.
*C07D 311/78* (2006.01)

(52) U.S. Cl.
USPC .......................................................... 549/382

(58) Field of Classification Search
USPC .......................................................... 549/382
See application file for complete search history.

(56) References Cited

U.S. PATENT DOCUMENTS

| | | | |
|---|---|---|---|
| 3,361,706 A | 1/1968 | Meriwether et al. |
| 3,562,172 A | 2/1971 | Ono et al. |
| 3,567,605 A | 3/1971 | Becker |
| 3,578,602 A | 5/1971 | Ono et al. |
| 4,215,010 A | 7/1980 | Hovey et al. |
| 4,342,668 A | 8/1982 | Hovey et al. |
| 4,637,698 A | 1/1987 | Kwak et al. |
| 4,816,584 A | 3/1989 | Kwak et al. |
| 4,818,096 A | 4/1989 | Heller et al. |
| 4,826,977 A | 5/1989 | Heller et al. |
| 4,880,667 A | 11/1989 | Welch |
| 4,931,219 A | 6/1990 | Kwiatkowski et al. |
| 4,931,220 A | 6/1990 | Haynes et al. |
| 5,066,818 A | 11/1991 | Gemert et al. |
| 5,238,931 A | 8/1993 | Yoshikawa et al. |
| 5,274,132 A | 12/1993 | VanGemert |
| 5,384,077 A | 1/1995 | Knowles |
| 5,405,958 A | 4/1995 | VanGemert |
| 5,466,398 A | 11/1995 | Van Gemert et al. |
| 6,068,797 A | 5/2000 | Hunt |
| 6,555,028 B2 | 4/2003 | Walters et al. |
| 2008/0103301 A1 | 5/2008 | Chopra et al. |

FOREIGN PATENT DOCUMENTS

| | | |
|---|---|---|
| WO | 9748762 A1 | 12/1997 |
| WO | 2004061047 A2 | 7/2004 |

OTHER PUBLICATIONS

Dorwald F. A. Side Reactions in Organic Synthesis, 2005, Wiley: VCH, Weinheim p. IX of Preface p. 1-15.*
Bickford et al. J. Oil Chemists' Soc. 1948 25, 251-4.*
Rust et al. Journal of Organic Chemistry, 1948, 3258-3258.*
Ochiai et al. Tetrahedron Letters, 1997, 38(22), 3927-3930.*
Challis et al. Chemistry of Amino Group, 1968 Chapter 6, Section C, on pp. 333-335.*
"Polymerization" in Hawley's Condensed Chemical Dictionary Thirteenth Edition, 1997, pp. 901-902, published by John Wiley & Sons, Inc., revised by Richard J. Lewis, Sr.

* cited by examiner

*Primary Examiner* — Nizal Chandrakumar
(74) *Attorney, Agent, or Firm* — The Webb Law Firm

(57) ABSTRACT

The present invention relates to a method of making indeno-fused naphthol materials, that involves, with some embodiments, forming an indanone acid intermediate, which can be represented by the following general Formula V,

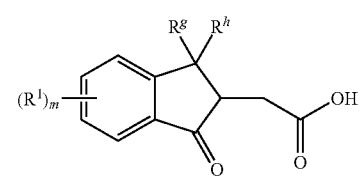

With Formula V, m is from 0 to 4, and $R^1$ for each m, $R^g$ and $R^h$ can each be independently selected from, for example, hydrogen and hydrocarbyl. The present invention also relates to a method of making an indeno-fused naphthopyran that involves an indanone acid intermediate synthetic route.

9 Claims, No Drawings

METHOD OF MAKING INDENO-FUSED NAPHTHOL MATERIALS

CROSS REFERENCE TO RELATED APPLICATIONS

This application claims the benefit of priority of U.S. Provisional Patent Application No. 61/459,617, filed Dec. 16, 2010, all of which document is hereby incorporated herein by reference.

FIELD OF THE INVENTION

The present invention relates to a method of making indeno-fused naphthol materials and related materials, such as photochromic indeno-fused naphthopyrans, that involves forming an indanone acid intermediate.

BACKGROUND OF THE INVENTION

Indeno-fused naphthol materials, including ethers and esters of indeno-fused naphthols, have many uses, such as intermediates in the synthesis of photochromic compounds and materials, such as indeno-fused naphthopyrans. Photochromic materials, such as indeno-fused naphthopyrans, in response to certain wavelengths of electromagnetic radiation (or "actinic radiation"), typically undergo a transformation from one form or state to another form, with each form having a characteristic or distinguishable absorption spectrum associated therewith. Typically, upon exposure to actinic radiation, many photochromic materials are transformed from a closed-form, which corresponds to an unactivated (or bleached, e.g., substantially colorless) state of the photochromic material, to an open-form, which corresponds to an activated (or colored) state of the photochromic material. In the absence of exposure to actinic radiation, such photochromic materials are reversibly transformed from the activated (or colored) state, back to the unactivated (or bleached) state. Compositions and articles, such as eyewear lenses, that contain photochromic materials or have photochromic materials applied thereto (e.g., in form of a photochromic coating composition) typically display colorless (e.g., clear) and colored states that correspond to the colorless and colored states of the photochromic materials contained therein or applied thereto.

Indeno-fused naphthol materials are typically prepared by a synthetic scheme involving the reaction of a benzophenone with a dialkyl succinate, which is typically referred to as a Stobbe reaction route. When unsymmetrical benzophenones are used, a mixture of indeno-fused naphthol materials typically results from the Stobbe reaction route. The mixture of indeno-fused naphthols typically must be separated so as to isolate the desired indeno-fused naphthol. The isolated indeno-fused naphthol can then be used in subsequent reactions (e.g., in the synthesis of photochromic indeno-fused naphthopyrans). The separation and isolation steps generally result in significantly reduced yields relative to the desired indeno-fused naphthol materials.

Some photochromic materials, such as photochromic indeno-fused naphthopyrans can be expensive, and in light of economic considerations, reducing the costs associated with synthesizing such materials is typically desirable.

It would be desirable to develop new methods of making indeno-fused naphthol materials. In addition, it would be desirable that such newly developed methods provide improved yields, and economic benefits relative to previous synthetic methods.

SUMMARY OF THE INVENTION

In accordance with the present invention, there is provided a method of making an indeno-fused naphthol material represented by the following Formula I,

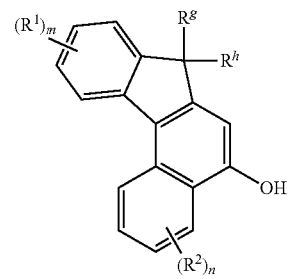

With reference to Formula I, m and n are each independently selected from 0 to 4. With further reference to Formula I, $R^1$ for each m, and $R^2$ for each n, are in each case independently selected from hydrocarbyl optionally interrupted with at least one of —O—, —S—, —C(O)—, —C(O)O—, —S(O)—, —SO$_2$—, —N($R_{11}'$)— where $R_{11}'$ is selected from hydrogen, hydrocarbyl or substituted hydrocarbyl, and combinations of two or more thereof; substituted hydrocarbyl optionally interrupted with at least one of —O—, —S—, —C(O)—, —C(O)O—, —S(O)—, —SO$_2$—, —N($R_{11}'$)— where $R_{11}'$ is selected from hydrogen, hydrocarbyl or substituted hydrocarbyl, and combinations of two or more thereof; halogen; cyano; and —N($R_{11}'$)$R_{12}'$, wherein $R_{11}'$ and $R_{12}'$ are each independently selected from hydrogen, hydrocarbyl or substituted hydrocarbyl, or $R_{11}'$ and $R_{12}'$ together form an aliphatic and/or aromatic ring structure (e.g., a single ring, polycyclic ring, or fused ring structure) optionally including at least one heteroatom. The $R^g$ and $R^h$ groups of Formula I are each independently selected from, hydrogen; hydrocarbyl optionally interrupted with at least one of —O—, —S—, —C(O)—, —C(O)O—, —S(O)—, —SO$_2$—, and —N($R_{11}'$)— where $R_{11}'$ is selected from hydrogen, hydrocarbyl or substituted hydrocarbyl; and substituted hydrocarbyl optionally interrupted with at least one of —O—, —S—, —C(O)—, —C(O)O—, —S(O)—, and —N($R^{11'}$)— where $R_{11}'$ is selected from hydrogen, hydrocarbyl or substituted hydrocarbyl; or $R^g$ and $R^h$ together form a ring structure optionally including at least one heteroatom.

The method of making the indeno-fused naphthol material represented by the Formula I comprises, (a) reacting an alkyl benzene represented by Formula II with maleic anhydride, thereby forming a succinic acid substituted intermediate represented by Formula III,

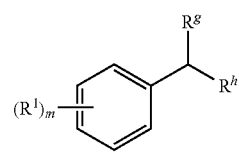

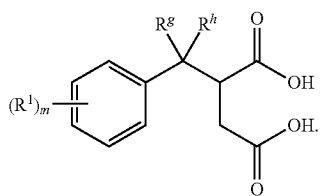

III

The method of the present invention further comprises, (b) converting the succinic acid substituted intermediate represented by Formula III to a succinic anhydride substituted intermediate represented by Formula IV,

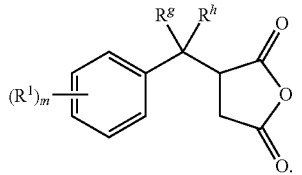

IV

The method of the present invention further comprises, (c) converting the succinic anhydride substituted intermediate represented by Formula IV to an indanone acid intermediate represented by Formula V,

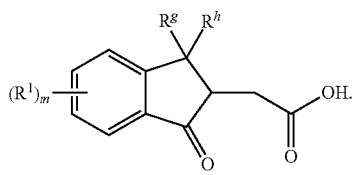

V

The method of the present invention further comprises, (d), reacting the indanone acid intermediate represented by Formula V with a nucleophile represented by Formula VI to form a substituted indanone intermediate represented by at least one of Formula VIIa, Formula VIIb and Formula VIIc,

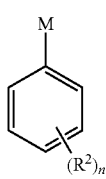

VI wherein M represents a counterion comprising a metal selected from Mg, Li, Cu and combinations thereof,

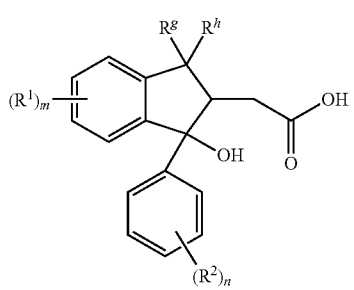

VIIa

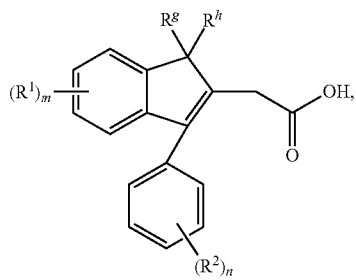

VIIb

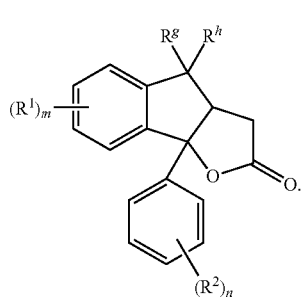

VIIc

The method of the present invention, still further comprises, (e) converting the substituted indanone intermediate represented by at least one of Formula VIIa, Formula VIIb and Formula VIIc to the indeno-fused naphthol represented by Formula I.

With Formulas II, III, IV, V, VI, VIIa, VIIb, and VIIc, m, $R^1$ n, $R^2$, $R^g$, and $R^h$ are in each case independently selected from those values, ranges, and groups as described above and further herein with reference to Formula I. Alternatively, one or more of $R^1$, $R^2$, $R^g$, and $R^h$ can in each case independently represent one or more precursors of the those groups as described above and further herein with reference to Formula I.

In accordance with the present invention, there is further provided a method of making an indeno-fused naphthopyran represented by the following Formula XI,

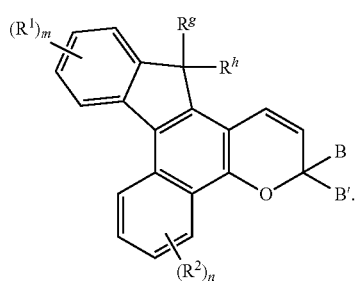

XI

With the indeno-fused naphthopyran represented by Formula XI, m, $R^1$, n, $R^2$, $R^g$, and $R^h$ are in each case independently selected from those values, ranges, and groups as described above and further herein with reference to Formula I, or in each case independently represent one or more precursors of the those groups as described above and further herein with reference to Formula I.

The B and B' groups of the indeno-fused naphthopyran represented by Formula XI are each independently selected from unsubstituted aryl, substituted aryl, unsubstituted heteroaryl, substituted heteroaryl, polyalkoxy, and polyalkoxy having a polymerizable group. Alternatively, B and B' taken together form a ring structure selected from unsubstituted fluoren-9-ylidene, substituted fluoren-9-ylidene, saturated spino-monocyclic hydrocarbon ring, saturated spiro-bicyclic hydrocarbon ring, and spiro-tricyclic hydrocarbon ring.

The method of making the indeno-fused naphthopyran represented by Formula XI, involves forming the indeno-fused naphthol material represented by Formula I as described above, and reacting the indeno-fused naphthol material represented by Formula I with a propargyl alcohol represented by the following Formula XI,

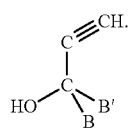

XII

With the propargyl alcohol represented by Formula XII, B and B' are each selected from those groups as described above and further herein with regard to Formula XI, or in each case independently represent one or more precursors of the those groups as described above and further herein with reference to Formula XI.

DETAILED DESCRIPTION OF THE INVENTION

As used herein and in the claims, the term "actinic radiation" means electromagnetic radiation that is capable of transforming a photochromic material from one form or state to another.

As used herein and in the claims, the term "photochromic" means having an absorption spectrum for at least visible radiation that varies in response to absorption of at least actinic radiation. Further, as used herein the term "photochromic material" means any substance that is adapted to display photochromic properties, i.e. adapted to have an absorption spectrum for at least visible radiation that varies in response to absorption of at least actinic radiation, and which, includes at least one photochromic compound.

As used herein and in the claims, molecular weight values of polymers, such as weight average molecular weights (Mw) and number average molecular weights (Mn), are determined by gel permeation chromatography using appropriate standards, such as polystyrene standards.

As used herein and in the claims, polydispersity index (PDI) values represent a ratio of the weight average molecular weight (Mw) to the number average molecular weight (Mn) of the polymer (i.e., Mw/Mn).

As used herein and in the claims, recitations of "linear or branched" groups, such as linear or branched alkyl, are understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein and in the claims, the term "halo" and similar terms, such as halo group, halogen, and halogen group means F, Cl, Br and/or I, such as fluoro, chloro, bromo and/or iodo.

Unless otherwise indicated, all ranges or ratios disclosed herein are to be understood to encompass any and all subranges or subratios subsumed therein. For example, a stated range or ratio of "1 to 10" should be considered to include any and all subranges between, (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein and in the claims, unless otherwise indicated, the symbol "Δ" means heat or thermal energy, such as heat introduced into and/or retained within a chemical reaction.

As used herein and in the claims, the term "precursor" and related terms, such as "precursors" with regard to the various groups, for example, $R^1$, $R^2$, $R^g$, $R^h$, B and B', of the compounds and intermediates described herein, for example, the indeno-fused naphthols represented by Formula I and the indeno-fused naphthopyrans represented by Formula XI, means a group that can be converted in one or more steps to the final or desired group. For purposes of non-limiting illustration: a precursor of a hydroxyl group (—OH) includes, but is not limited to, a carboxylic acid ester group (—OC(O)R where R is hydrogen or an optionally substituted hydrocarbyl); and a precursor of a carboxylic acid ester group (—OC(O)R) includes, but is not limited to, a hydroxyl group (—OH), which can be reacted, for example, with a carboxylic acid halide, such as acetic acid chloride (or acetyl chloride).

As used herein and in the claims, unless otherwise indicated, left-to-right representations of linking groups, such as divalent linking groups, are inclusive of other appropriate orientations, such as, right-to-left orientations. For purposes of non-limiting illustration, the left-to-right representation of the divalent linking group —C(O)O—, is inclusive of the right-to-left representation thereof, —O(O)C—.

As used herein and in the claims, the articles "a," "an," and "the" include plural referents unless otherwise expressly and unequivocally limited to one referent.

Other than in the operating examples, or where otherwise indicated, all numbers expressing quantities of ingredients, reaction conditions, and so forth used in the specification and claims are to be understood as modified in all instances by the term "about."

The method of the present invention involves making an indeno-fused naphthol, material represented by Formula I. The $R^1$, $R^2$, $R^g$ and $R^h$ groups of the indeno-fused naphthol material represented by Formula I, can in each case be selected from hydrocarbyl, and substituted hydrocarbyl.

As used herein and in the claims the term "hydrocarbyl" and similar terms, such as "hydrocarbyl substituent," means: linear or branched $C_1$-$C_{20}$ alkyl (e.g., linear or branched $C_1$-$C_{10}$ alkyl); linear or branched $C_2$-$C_{20}$ alkenyl (e.g., linear or branched $C_2$-$C_{10}$ alkenyl); linear or branched $C_2$-$C_{20}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_{12}$ heterocycloalkyl (having at least one hetero atom in the cyclic ring); $C_5$-$C_{18}$ aryl (including polycyclic aryl groups) (e.g., $C_5$-$C_{10}$ aryl); $C_5$-$C_{18}$ heteroaryl (having at least one hetero atom in the aromatic ring); and $C_6$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to tetrahydrofuranyl, tetrahydropyranyl and piperidinyl. Representative aryl groups include but are not limited to phenyl and naphthyl. Representative heteroaryl groups include but are not limited to furanyl, pyranyl and pyridinyl. Representative aralkyl groups include but are not limited to benzyl, and phenethyl.

The term "substituted hydrocarbyl" as used herein and in the claims means a hydrocarbyl group in which at least one hydrogen thereof has been substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl, alkenyl, alkynyl, cycloalkyl, heterocycloalkyl, aryl, heteroaryl, and aralkyl groups), and amine groups, such as —N($R_{11}'$)($R_{12}'$) where $R_{11}'$ and $R_{12}'$ are each independently selected from hydrogen, hydrocarbyl and substituted hydrocarbyl.

The term "substituted hydrocarbyl" is inclusive of halohydrocarbyl (or halo substituted hydrocarbyl) substituents. The term "halohydrocarbyl" as used herein and in the claims, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom being replaced by a halogen atom (e.g., a fluoromethyl group) to full halogenation (perhalogenation) in which all replaceable hydrogen atoms on the hydrocarbyl group have been replaced by a halogen atom (e.g., trifluoromethyl or perfluoromethyl). Correspondingly, the term "perhalohydrocarbyl group" as used herein and in the claims means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which $R^1$, $R^2$, $R^g$, and $R^h$ can each be selected, can in each case be independently and optionally interrupted with at least one of —O—, —S—, —C(O)—, —C(O)O—, —S(O)—, —$SO_2$—, —N($R_{11}'$)—. As used herein and in the claims, by interrupted with at least one of —O—, —S—, —C(O)—, —C(O)O—, —S(O)—, —$SO_2$—, —N($R_{11}'$)—, means that at least one carbon of, but less than all of the carbons of, the hydrocarbyl group or substituted hydrocarbyl group, is in each case independently replaced with one of the recited divalent non-carbon linking groups. The hydrocarbyl and substituted hydrocarbyl groups can be interrupted with two, or more of the above recited linking groups, which can be adjacent each other or separated by one or more carbons.

The various groups of the indeno-fused naphthol materials, intermediates and indeno-fused naphthopyrans prepared and used in accordance with the methods of the present invention, will be described in further detail herein.

The method of making or synthesizing the indeno-fused naphthol represented by Formula I, according to the present invention, involves forming a succinic acid substituted intermediate represented by Formula III, by reacting an alkyl benzene represented by Formula II with maleic anhydride. The reaction is typically conducted in the presence of a free radical generator, such as a peroxide, and under appropriate conditions, such as with reflux, as represented in the following Scheme 1.

Scheme 1

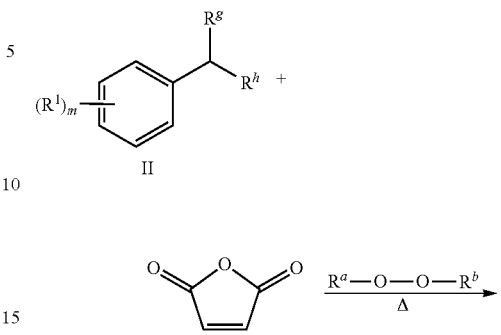

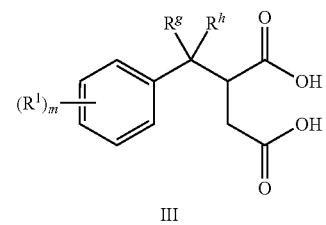

The peroxide of Scheme-1 is typically a bishydrocarbyl peroxide represented by the formula, $R^a$—O—O—$R^b$, in which the $R^a$ and $R^b$ groups can each be independently selected from hydrocarbyl and substituted hydrocarbyl, such as linear or branched $C_1$-$C_{10}$ alkyl or linear or branched $C_1$-$C_5$ alkyl (e.g., methyl, ethyl, n-propyl, iso-propyl, n-butyl, iso-butyl, and tert-butyl). With some embodiments of the present invention, $R^a$ and $R^b$ of the peroxide of Scheme 1 are each selected from tert-butyl. The reflux can be conducted under appropriated conditions, including, for example reduced pressure, ambient pressure, and/or elevated pressure. Typically, the reflux under which the succinic acid substituted intermediate represented by Formula III is formed, is conducted under conditions of ambient pressure (e.g., approximately 1 atm), under an inert atmosphere (e.g., under a nitrogen sweep), and elevated temperature, such as from 50° C. to 200° C., or from 60° C. to 180° C., or from 80° C. to 150° C.

The alkyl benzene represented by Formula II can be used as both a reagent and a solvent in the reaction represented by Scheme 1, and/or a separate non-reactive solvent can be present. Typically, after completion of the reaction, solvent and excess alkyl benzene, if present, is removed by reduced pressure stripping, leaving crude succinic acid substituted intermediate represented by Formula III within the reaction vessel. The crude succinic acid substituted intermediate represented by Formula III can be further isolated or otherwise purified in accordance with art recognized methods, or used in its crude form in the next step of the synthetic sequence.

In the next step of the method of the present invention, the succinic acid substituted intermediate represented by Formula III is converted to a succinic anhydride substituted intermediate represented by Formula IV. The conversion is typically conducted in the presence of a Brønsted acid (or protonic acid), such as a sulfonic acid, and under appropriate conditions, such as with reflux, as represented in the following Scheme 2.

Scheme-2

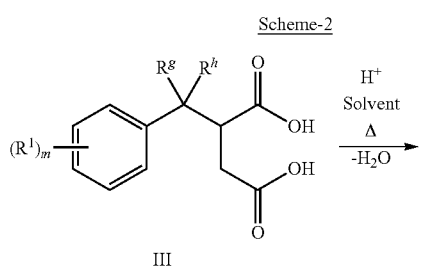

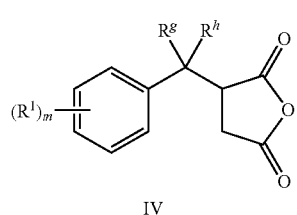

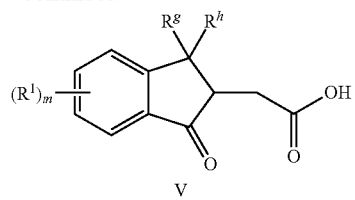

With reference to Scheme-2, the Brønsted acid (represented by H+) is typically a strong acid, such as a sulfonic acid (e.g., dodecyl benzene sulfonic acid, DBSA). With some embodiments, a heterogeneous catalyst can be used in the reaction represented by Scheme-2. Examples of heterogeneous catalysts include, but are not limited to, sulfonic acid functional perhalogenated olefins, such as sulfonic acid functional polytetrafluoroethylene available under the tradename NAFION H available commercially from E.I. du Pont de Nemours & Co., Inc. The solvent can be selected from any suitable solvent from which the anhydride product IV can be separated, such as xylene. The reflux can be conducted under art-recognized conditions, such as described with regard to Scheme-1 above. As the reaction/conversion progresses, water is removed from the reaction vessel, and typically collected and measured. Typically, after completion of the reaction, solvent is removed by reduced pressure stripping, leaving crude succinic anhydride substituted intermediate represented by Formula IV within the reaction vessel. The crude succinic anhydride substituted intermediate represented by Formula IV can be further isolated or otherwise purified in accordance with art recognized methods, or used in its crude form in the next step of the synthetic sequence.

The succinic anhydride substituted intermediate represented by Formula IV is next converted to an indanone acid intermediate represented by Formula V, in the next step of the method of the present invention, as represented by the following Scheme-3.

Scheme-3

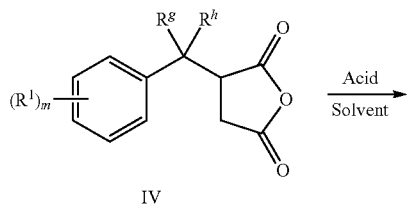

The conversion of the succinic anhydride substituted intermediate represented by Formula IV to the indanone acid intermediate represented by Formula V, represented by Scheme-3, is typically conducted in the presence of an acid, such as one or more Lewis acids and/or one or more Brønsted acids. Examples of acids that can be used in the conversion represented by Scheme-3 include, but are not limited to: aluminum chloride ($AlCl_3$); tin chloride ($SnCl_4$); $Bi(OTf)_3$ (bismuth tris-triflate); at least one phosphoric acid, including but not limited to orthophosphoric acid ($H_3PO_4$) and/or polyphosphoric acid; and combinations thereof. With some embodiments of the present invention, the conversion represented by Scheme-3 is performed in the presence of a Lewis acid, such as aluminum chloride ($AlCl_3$). The conversion represented by Scheme-3 is typically conducted in the presence of an appropriate solvent, such as a halogenated solvent, from which the indanone acid intermediate V can be separated. Examples of halogenated solvents include, but are not limited to halogenated $C_1$-$C_6$ alkanes, such as dichloromethane (DCM). The conversion represented by Scheme-3 is also typically conducted under conditions of ambient pressure (e.g., approximately 1 atm), under an inert atmosphere (e.g., under a nitrogen sweep), and an appropriate temperature, such as from −15° C. to 50° C., or from −10° C. to 40° C., or from 0° C. to 30° C. Conversion of the succinic anhydride substituted intermediate represented by Formula IV to the indanone acid intermediate represented by Formula V, as represented by Scheme-3, is typically referred to an intramolecular Friedel-Crafts reaction.

The conversion represented by Scheme-3 typically results in the formation of a mixture of materials, from which the indanone acid intermediate represented by Formula V is typically isolated. Isolation of the indanone acid intermediate represented by Formula V can be conducted in accordance with art-recognized methods. With some embodiments of the present invention, the indanone acid intermediate represented by Formula V is isolated by chromatography, in accordance with art-recognized methods.

In the next step of the method of the present invention, the indanone acid intermediate represented by Formula V is reacted with a nucleophile represented by Formula VI to form a substituted indanone intermediate represented by at least one of Formula VIIa, Formula VIIb and Formula VIIc, as represented by the following Scheme-4.

Scheme-4

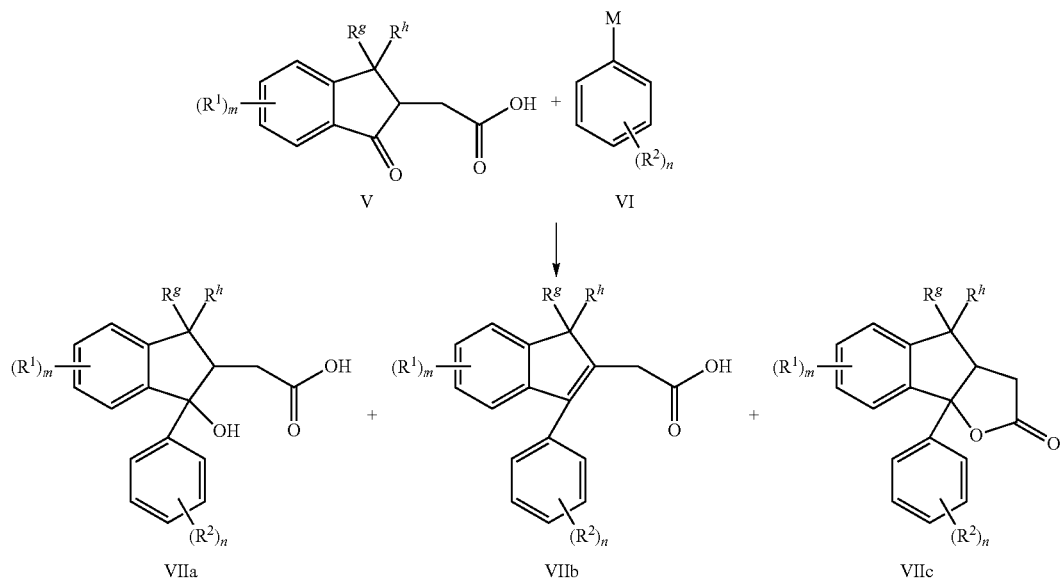

As discussed previously herein, M of the nucleophile represented by Formula VI, represents a counterion, and in particular a cation, that includes a metal selected from Mg, Li, Cu, and combinations of two or more thereof. Typically, the counterion M also includes a halogen, and can be represented by $MX^+$. With some embodiments of the present invention, the counterion M includes Mg and a halogen, such as Cl (e.g., $MgCl^+$).

With some embodiments of the present invention, the nucleophile represented by Formula VI is a Grignard reagent, and the reaction represented by Scheme-4 is a Grignard reaction, which is conducted under Grignard reaction conditions. The reaction represented by Scheme-4 is typically conducted in the presence of an appropriate solvent, such as tetrahydrofuran (THF), and under conditions of ambient pressure (e.g., approximately 1 atm), under an inert atmosphere (e.g., under a nitrogen sweep), an appropriate temperature, such as from −80° C. to 80° C., or from −20° C. to 60° C., or from 0° C. to 20° C., and optionally at elevated temperature, such as under reflux conditions.

With further reference to Scheme-4, the carboxylic acid group of the indanone acid intermediate represented by Formula V typically deactivates a molar equivalent of the nucleophile represented by Formula VI. To address this deactivation, additional nucleophile represented by Formula VI is added to the reaction vessel. With some embodiments, for every mole of indanone acid intermediate represented by Formula V, two moles of nucleophile represented by Formula VI are added to or present within the reaction vessel. With further embodiments of the present invention, the carboxylic acid group of the indanone acid intermediate is protected, for example converted to an oxazoline group, as will be discussed in further detail herein.

The substituted indanone intermediate represented by at least one of Formula VIIa, Formula VIIb and Formula VIIc can be isolated in accordance with art-recognized methods, or used in a crude form in the next step of the method of the present invention. The substituted indanone intermediate represented by at least one of Formula VIIa, Formula VIIb and Formula VIIc is typically isolated and optionally further purified (e.g., by art-recognized column chromatography methods) before the next step of the synthetic method.

The substituted indanone intermediate represented by at least one of Formula VIIa, Formula VIIb and Formula VIIc is converted to the indeno-fused naphthol represented by Formula I, in the next step of the method of the present invention. This conversion can be conducted in substantially one step in the presence of a Brønsted acid, as represented by the following Scheme-5.

Scheme-5

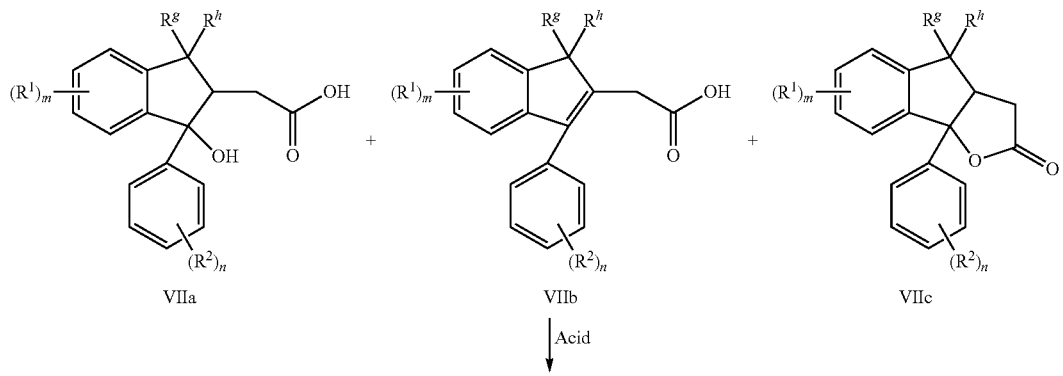

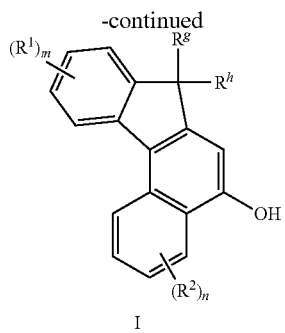

The conversion/reaction represented by Scheme-5 is typically conducted under conditions of elevated temperature, for example at a temperature from 20° C. to 200° C., or from 50° C. to 150° C., or from 80° C. to 120° C., under conditions of ambient pressure (e.g., approximately 1 atm), and under an inert atmosphere, such as a nitrogen sweep. Examples Of Brønsted acids that can be used in the conversion represented by Scheme-5 include, but are not limited to, carboxylic acids (e.g., acetic, proponoic, and/or butanoic acid), sulfonic acids (e.g., R—S(O)(O)—OH, where R is selected from hydrocarbyl or substituted hydrocarbyl, such as perhalohydrocarbyl), phosphoric acids (e.g., orthophosphoric acid, one or more polyphosphoric acids, and/or related combinations thereof), and combinations thereof. The Brønsted acid can be present in a catalytic amount, equimolar amount or excess amount, depending in part on the selection of Brønsted acid(s), such as from 0.01 to 50 moles, based on total moles of substituted indanone intermediate represented by at least one of Formulas VIIa, VIIb and VIIc.

With some embodiments of the present invention, conversion of the substituted indanone intermediate represented by at least one of Formula VIIa, Formula VIIb and Formula VIIc to the indeno-fused naphthol represented by Formula I, is conducted in two steps. Initially an indeno-fused naphtho-intermediate represented by Formula X is formed, which is then reacted with a Brønsted acid so as to form the indeno-fused naphthol represented by Formula I, as represented by the following Scheme-6.

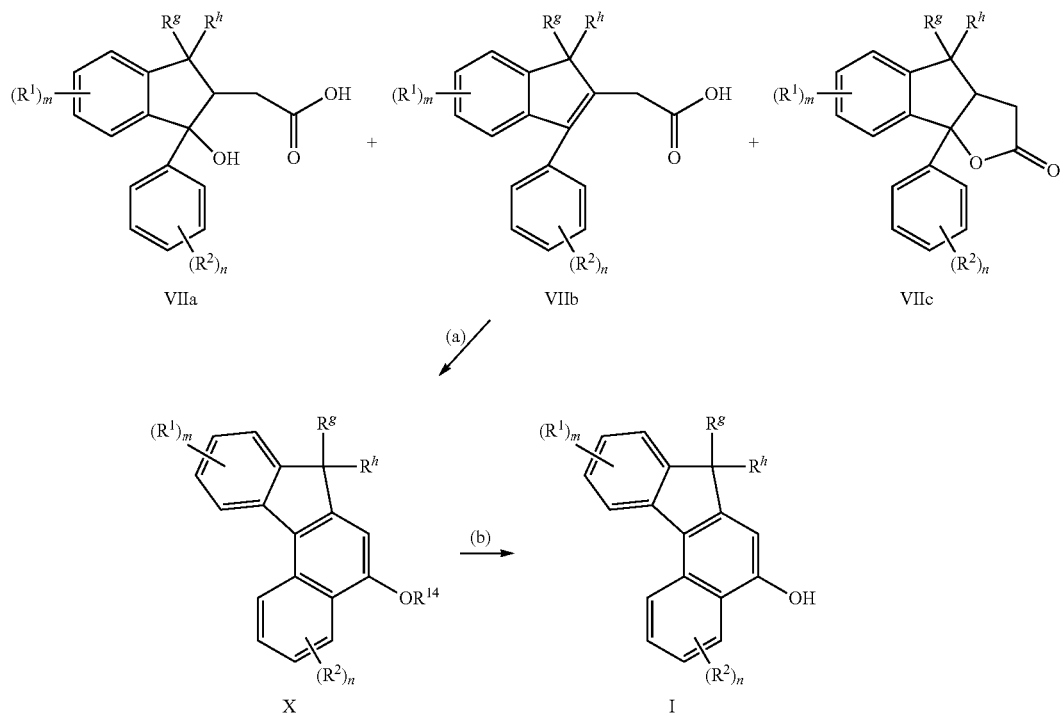

With reference to Scheme-6, the $R^{14}$ group of the indeno-fused naphtho-intermediate represented by Formula X is selected from —C(O)—$R^{15}$ and —S(O)(O)$R^{15}$, where $R^{15}$ in each case is independently selected from hydrocarbyl (e.g., $C_1$-$C_{10}$ alkyl) and halohydrocarbyl (e.g., $C_1$-$C_{10}$ perhaloalkyl).

The initial conversion or reaction of step-(a) of Scheme-6, is typically conducted in the presence of a material selected from carboxylic acid halide, carboxylic acid anhydride, sulfonyl halide, sulfonyl anhydride and combinations thereof. The carboxylic acid halide, carboxylic acid anhydride and/or sulfonyl halide is typically present in at least an equimolar amount relative to the substituted indanone intermediate represented by at least one of Formulas VIIa, VIIb and VIIc. Carboxylic acid halides that can be used in step-(a), can be represented by the structure, $R^c$—C(O)—X, where $R^c$ is selected from hydrocarbyl or substituted hydrocarbyl, and X is selected from halogen (e.g., Cl). Sulfonyl halides that can be used in step-(a), can be represented by the structure, $R^c$—S(O)(O)—X, where $R^c$ is selected from hydrocarbyl or substituted hydrocarbyl, and X is selected from halogen (e.g., Cl). Sulfonyl anhydrides that can be used in step-(a), can be represented by the structure, $R^d$—S($O_2$)—O—($O_2$)S—$R^e$ where $R^d$ and $R^e$ are each independently selected from hydrogen, hydrocarbyl, and substituted hydrocarbyl (e.g., halohydrocarbyl, such as $C_1$-$C_{10}$ perhaloalkyl, e.g., —$CF_3$). Carboxylic acid anhydrides that can be used in step-(a), can be represented by the structure, $R^d$—C(O)—O—C(O)—$R^e$, where $R^d$ and $R^e$ are each independently selected from hydrogen, hydrocarbyl, and substituted hydrocarbyl (e.g., halohydrocarbyl, such as $C_1$-$C_{10}$ perhaloalkyl, e.g., —$CF_3$).

The initial conversion or cyclization reaction of step-(a) of Scheme-6, can alternatively be conducted in the presence of a suitable catalyst. With some embodiments of the present invention, step-(a) of Scheme-6 is conducted in the presence of a catalytic amount of Bi($SO_3CF_3$)$_3$, which can be present in an amount of from 0.01 to 0.01 moles, based on total moles of substituted indanone intermediate represented by at least one of Formulas VIIa, VIIb, and VIIc.

The indeno-fused naphtho-intermediate represented by Formula X is converted to the indeno-fused naphthol represented by Formula I in step-(b) of Scheme-6 in the presence of a Brønsted acid. The Brønsted acid can be selected from hydrogen halides (HX, where X is halogen) such as HCl, and/or carboxylic acids. The Brønsted acid is typically present in an excess amount relative to the amount of indeno-fused naphtho-intermediate represented by Formula X. For example the conversion of step-(b) can be conducted in the presence of concentrated hydrogen halide acid, such as concentrated HCl. The conversion of step-(b) is typically conducted in the presence of a solvent, such as methanol, under conditions of elevated temperature, for example at a temperature from 20° C. to 200° C., or from 50° C. to 150° C., or from 80° C. to 120° C., under conditions of ambient pressure (e.g., approximately 1 atm), and under an inert atmosphere, such as a nitrogen sweep.

Depending on the ring-position, identity and number of the $R^2$ group(s) of the substituted indanone intermediate represented by at least one of Formulas VIIa, VIIb and VIIc, a mixture of indeno-fused naphthols represented by Formula I can be obtained in the method of the present invention. One or more of the structural isomers of the mixture of indeno-fused naphthols can be isolated in accordance with art-recognized methods, such as chromatographic methods. Alternatively, the mixture of indeno-fused naphthols can be left unresolved.

For purposes of illustration, when $R^g$ and $R^h$ are each methyl (—$CH^3$), m is zero, n is 1, and $R^2$ is a methoxy group (—$OCH_3$) located at position-3 of the ring of the substituted indanone intermediate represented by at least one of Formulas VIIa, VIIb and VIIc, the method of the present invention can result in the formation of two structural isomers of the indeno-fused naphthol, as represented by the following Formulas Ia and Ib.

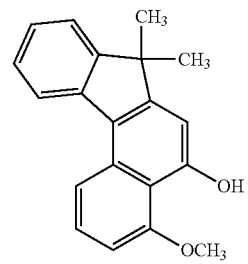

Ia

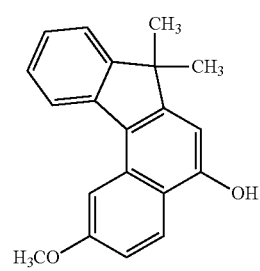

Ib

The indeno-fused naphthols represented by Formulas Ia and Ib can be present in a wide range of relative amounts. For example the indeno-fused naphthol represented by Formula Ia can be present in an amount of from 1 to 99 mole percent, or from 20 to 80 mole percent, or from 30 to 70 mole percent, and the indeno-fused naphthol represented by Formula Ib can be present in an amount of from 1 to 99 mole percent, or from 20 to 80 mole percent, or from 30 to 70 mole percent, based in each case on total moles of indeno-fused naphthol represented by Formula Ia and Ib. With some embodiments, the indeno-fused naphthol represented by Formula Ia can be present in an amount of from 15 to 35 mole percent (e.g., about 30 mole percent), and the indeno-fused naphthol represented by Formula Ib can be present in an amount of from 65 to 85 mole percent (e.g., about 70 mole percent), in each case based on total moles of indeno-fused naphthol represented by Formula Ia and Ib.

The method of the present invention can result in the formation of indeno-fused naphthols represented by Formula I in a wide range of yields. For example the method of the present invention can result in the formation of indeno-fused naphthols represented by Formula I yields of from 1 to 85 mole percent, based on theoretical moles of indeno-fused naphthol that could be produced. Typically, the method of the present invention results in the formation of indeno-fused naphthols in yields of at least 50 mole percent, such as from 50 to 85 mole percent, or from 60 to 75 mole percent, based on theoretical moles of indeno-fused naphthol that could be produced.

With some embodiments of the present invention, the carboxylic acid group of the indanone acid intermediate represented by Formula V, can be protected so as to minimize or prevent reaction between the protected carboxylic acid group and the nucleophile represented by Formula VI. With some embodiments, the indanone acid intermediate represented by Formula V is converted to an indanone oxazoline intermediate represented by the following Formula VIII.

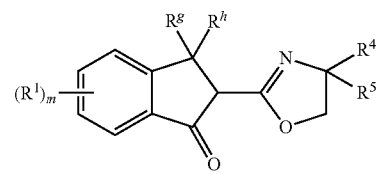

VIII

With reference to the indanone oxazoline intermediate represented by Formula VIII, m, $R^1$, $R^g$, and $R^h$ are in each case independently selected from those values, ranges, and groups as described above and further herein with reference to Formula I, or in each case independently represent one or more precursors of those groups as described above and further herein with reference to Formula I. With further reference to Formula VIII, $R^4$ and $R^5$ are each independently selected from hydrogen, hydrocarbyl and substituted hydrocarbyl.

The indanone oxazoline intermediate represented by Formula VIII can be formed by suitable methods. With some embodiments, the indanone oxazoline intermediate represented by Formula VIII can be formed by reaction of the indanone acid intermediate represented by Formula V with an amino alcohol, such as 2-amino-2-methyl-3-hydroxy propane, as represented by the following Scheme-7.

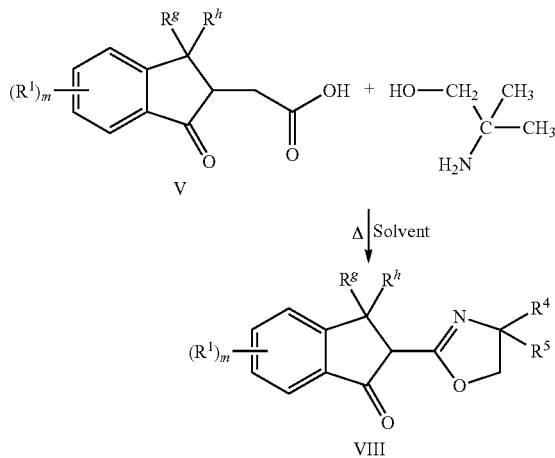

The reaction depicted in Scheme-7 is typically conducted in the presence of a suitable solvent, such as xylene, and under appropriate reflux conditions.

The indanone oxazoline intermediate represented by Formula VIII can alternatively be formed by a multi-step synthetic scheme that involves the formation of a carboxylic acid halide intermediate, as represented by the following Scheme-8.

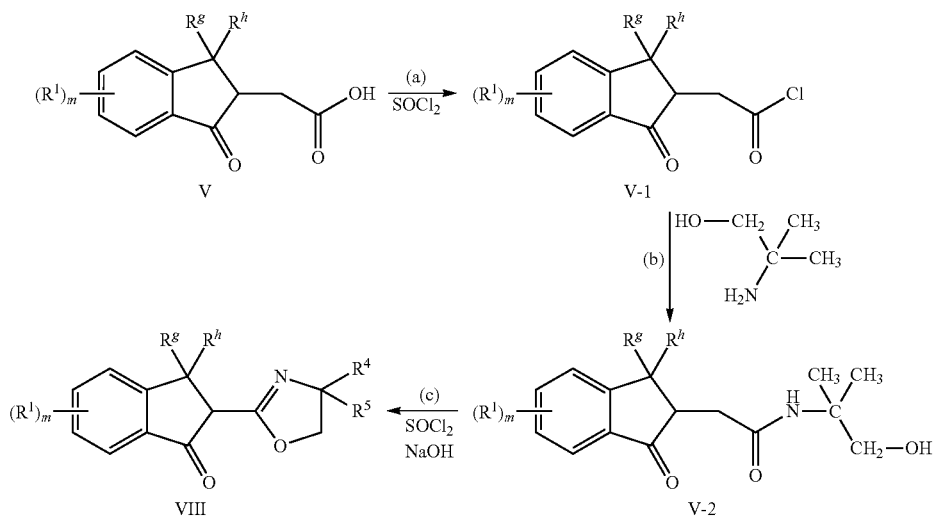

In step-(a) of Scheme-8, thionyl chloride ($SOCl_2$) is reacted with the indanone acid intermediate represented by Formula V under art-recognized conditions, which results in formation of an indanone acid chloride intermediate represented by Formula V-1. The indanone acid chloride intermediate represented by Formula V-1 is then reacted in step-(b) with an amino alcohol, such as 2-amino-2-methyl-3-hydroxy propane, which results in the formation of the indanone hydroxyl functional amide intermediate represented by Formula V-2. In step-(c), the indanone hydroxyl functional amide intermediate represented by Formula V-2 is cyclized to form the indanone oxazoline intermediate represented by Formula VIII in the presence of thionyl chloride and base, such as sodium hydroxide.

The indanone oxazoline intermediate represented by Formula VIII is reacted with the nucleophile represented by Formula VI, so as to form a substituted indanone oxazoline intermediate represented by at least one of the following Formulas IXa and IXb.

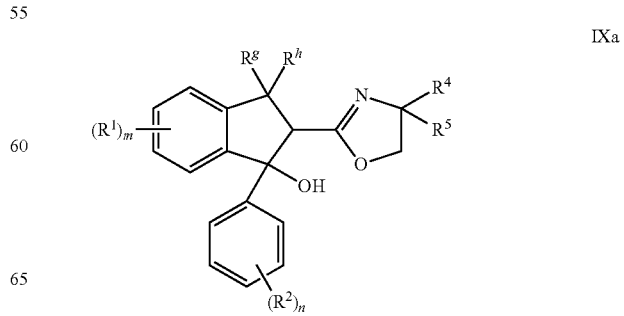

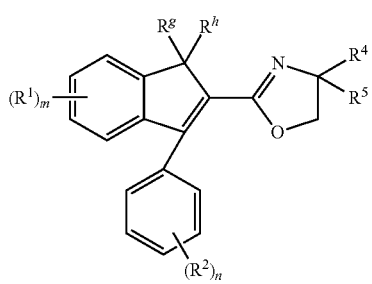

IXb

The reaction of the indanone oxazoline intermediate represented by Formula VIII with the nucleophile represented by Formula VI, so as to form the substituted indanone oxazoline intermediate represented by at least one of Formulas IXa and IXb, can be conducted in accordance with the description provided previously herein with regard to Scheme-4. Typically, however, an excess of the nucleophile represented by Formula VI, is not required when reacted with the indanone oxazoline intermediate represented by Formula VIII. With some embodiments, a substantially equimolar amount of nucleophile represented by Formula VI is reacted with the indanone oxazoline intermediate represented by Formula VIII.

The substituted indanone oxazoline intermediate represented by at least one of Formulas IXa and IXb is then converted to the substituted indanone intermediate represented by at least one of Formulas VIIa, VIIb and VIIc. More particularly, the oxazoline group is removed from the substituted indanone oxazoline intermediate represented by at least one of Formulas IXa and IXb, thus resulting in formation of the substituted indanone intermediate represented by at least one of Formulas VIIa, VIIb and VIIc, as represented by the following Scheme-9.

With reference to Scheme-9, removal of the oxazoline group is typically conducted in the presence of a Brønsted acid, and in particular an inorganic acid, such as concentrated HCl, and under appropriate reflux conditions. Appropriate work-up of the resulting substituted indanone intermediate represented by at least one of Formulas VIIa, VIIb and VIIc is typically conducted, for example to remove the amino alcohol and/or salt thereof.

After removal of the oxazoline group as represented in Scheme-9, and appropriate work-up, the substituted indanone intermediate represented by at least one of Formulas VIIa, VIIb and VIIc is then converted to the indeno-fused naphthol represented by Formula I, in accordance with the description provided previously herein.

The indeno-fused naphthols prepared by the method of the present invention can be used in numerous applications, such as additives in compositions, or as intermediates in the synthesis of additional compounds, such as non-photochromic (or static) dyes and photochromic dyes. Embodiments of the present invention also include a method of making an indeno-fused naphthopyran represented by Formula XI, which involves forming the indeno-fused naphthol represented by Formula I, as described previously herein, and then reacting the indeno-fused naphthol with a propargyl alcohol represented by Formula XII. Reaction of the indeno-fused naphthol represented by Formula I and the propargyl alcohol represented by Formula XII can be represented by the following Scheme-10.

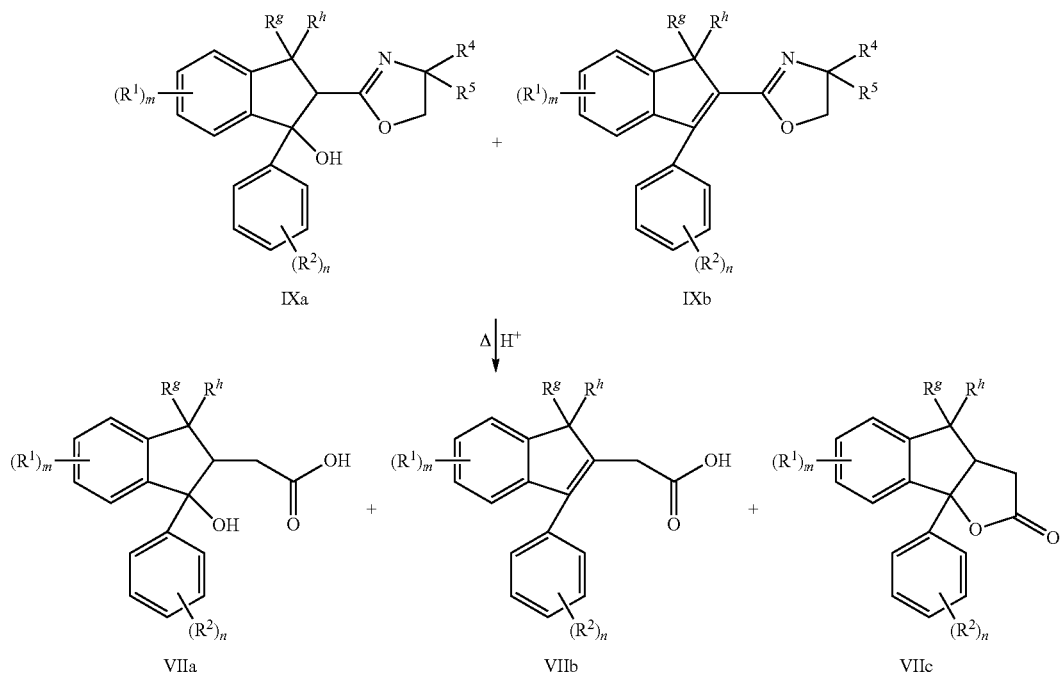

Scheme-9

Scheme-10

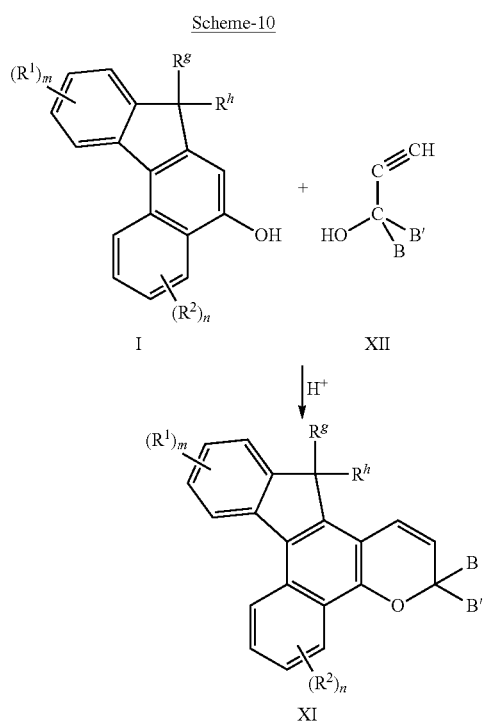

With reference to Scheme-10, the indeno-fused naphthol represented by Formula I is reacted or coupled with the propargyl alcohol represented by Formula XII in the presence of a catalytic amount of a Brønsted acid, such as dodecyl benzene sulfonic acid (DDBSA) or para-toluene sulfonic acid (pTSA), in a suitable solvent, such as a haloalkane (e.g., trichloromethane), under an inert atmosphere (e.g., a nitrogen sweep), and at an appropriate temperature, for example, from 0° C. to 150° C., or from 10° C. to 100° C., or from 20° C. to 80° C.

The groups and substituents of the indeno-fused naphthol represented by Formula I, the indeno-fused naphthopyran represented by Formula XI, and the compounds and intermediates used in their preparation, are described in further detail as follows. With some embodiments of the present invention, $R^1$ for each m, and $R^2$ for each n, are in each case independently selected from: a reactive substituent; a compatiblizing substituent; hydrogen; fluoro; chloro; $C_1$-$C_6$ alkyl; $C_3$-$C_7$ cycloalkyl; substituted or unsubstituted phenyl; —$OR_{10}'$ or —$OC(=O)R_{10}'$, wherein $R_{10}'$ is hydrogen, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$) alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl. The phenyl substituents (i.e., the substituents of the substituted phenyl) may be selected from hydroxyl, halogen, carbonyl, $C_1$-$C_6$ alkoxycarbonyl, cyano, halo($C_1$-$C_6$)alkyl, $C_1$-$C_6$ alkyl or $C_1$-$C_6$ alkoxy.

Alternatively or in addition to the previously recited classes and examples, $R^1$ for each m, and $R^2$ for each n, are in each case independently selected from: —$N(R_{11}')R_{12}'$, wherein $R_{11}'$ and $R_{12}'$ are each independently hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_8$ alkoxyalkyl, wherein the aryl group is phenyl or naphthyl, or $R_{11}'$ and $R_{12}'$ come together with the nitrogen atom to form a $C_3$-$C_{20}$ hetero-bicycloalkyl ring or a $C_4$-$C_{20}$ hetero-tricycloalkyl ring.

Further alternatively or in addition to the previously recited classes and examples, $R^1$ for each m, and $R^2$ for each n, can in each case be independently selected from, a nitrogen containing ring substituent represented by the following general (or graphic) formula XIIIA:

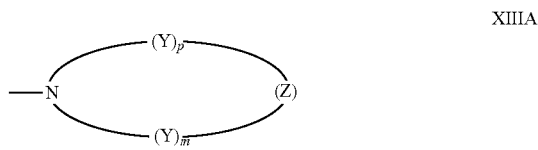

XIIIA

With the nitrogen ring substituent represented by general formula XIIIA, each —Y— is independently chosen for each occurrence from —$CH_2$—, —$CH(R_{13}')$—, —$C(R_{13}')_2$—, —CH(aryl)-, —$C(aryl)_2$-, and —$C(R_{13}')(aryl)$-, and Z is —Y—, —S—, —S(O)—, —$SO_2$—, —NH—, —$N(R_{13}')$—, or —N(aryl)-, wherein each $R_{13}'$ is independently $C_1$-$C_6$ alkyl, each aryl is independently phenyl or naphthyl, in is an integer 1, 2 or 3, and p is an integer 0, 1, 2, or 3, provided that when p is 0, Z is —Y—.

Additionally or alternatively, $R^1$ for each m, and $R^2$ for each n, can in each case also be independently selected from a nitrogen containing ring substituent represented by general formula XIIIB and/or general formula XIIIC:

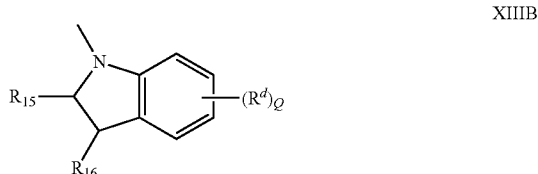

XIIIB

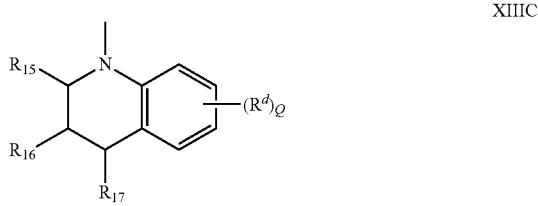

XIIIC

For the nitrogen containing ring substituents represented by general formulas XIIIB and XIIIC, $R_{15}$, $R_{16}$, and $R_{17}$ are each independently selected from hydrogen, $C_1$-$C_6$ alkyl, phenyl, or naphthyl, or the groups $R_{15}$ and $R_{16}$ together form a ring of 5 to 8 carbon atoms and each $R^d$ is independently for each occurrence selected from $C_1$-$C_6$ alkyl, $C_1$-$C_6$ alkoxy, fluoro or chloro, and Q is an integer 0, 1, 2, or 3.

Further alternatively or additionally, $R^1$ for each m, and $R^2$ for each n, can in each case also be independently selected from unsubstituted, mono-, or di-substituted $C_4$-$C_{18}$ spirobicyclic amine, or unsubstituted, mono-, and di-substituted $C_4$-$C_{18}$ spirotricyclic amine. The substituents of the spirobicyclic amines and the spirotricyclic amines may in each case be independently selected from aryl, $C_1$-$C_6$ alkyl, $C_1$-$C_6$ alkoxy, or phenyl($C_1$-$C_6$)alkyl.

With some embodiments of the present invention, two adjacent $R^1$ groups, and/or two adjacent $R^2$ groups, can together form a group represented by the following general formula XIIID or general formula XIIIE,

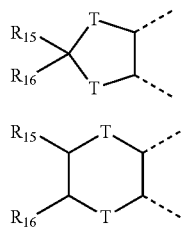

XIIID

XIIIE

With the groups represented by general formulas XIIID and XIIIE, T and T' are each independently oxygen or the group —NR$_{11}$—, where R$_{11}$, R$_{15}$, and R$_{16}$ are each as set forth and described previously herein.

The R$^g$ and R$^h$ groups with some embodiments of the present invention, can each be independently selected from: a reactive substituent; a compatiblizing substituent; hydrogen; hydroxy; C$_1$-C$_6$ alkyl; hydroxy(C$_1$-C$_6$)alkyl; C$_3$-C$_7$ cycloalkyl; allyl; substituted or unsubstituted phenyl; substituted or unsubstituted benzyl; chloro; fluoro; the group —C(=O)W', wherein W' is hydrogen, hydroxy, C$_1$-C$_6$ alkyl, C$_1$-C$_6$ alkoxy, the unsubstituted, mono- or di-substituted aryl groups phenyl or naphthyl-, phenoxy, mono- or di-(C$_1$-C$_6$) alkoxy substituted phenoxy, mono- or di-(C$_1$-C$_6$)alkoxy substituted phenoxy, amino, mono(C$_j$—C$_6$)alkylamino, di(C$_1$-C$_6$)alkylamino, phenylamino, mono- or di-(C$_1$-C$_6$)alkyl substituted phenylamino, or mono- or di-(C$_1$-C$_6$)alkoxy substituted phenylamino. The phenyl, benzyl, or aryl group substituents (e.g., the substituents of the substituted phenyl, substituted benzyl and substituted aryl groups) are each independently selected from C$_1$-C$_6$ alkyl or C$_1$-C$_6$ alkoxy.

The R$^g$ and R$^h$ groups with some embodiments of the present invention, can also each be independently selected from an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl or indolyl; each of said group substituents in (ii) being chosen independently for each occurrence from chloro, fluoro, C$_1$-C$_6$ alkyl or C$_1$-C$_6$ alkoxy.

The R$^g$ and R$^h$ groups can also, with some embodiments of the present invention, each be independently selected from a mono-substituted phenyl, in which the phenyl has a substituent located at the para position thereof, which is a linking group, —(CH$_2$)$_t$— or —O—(CH$_2$)$_t$—, that is connected to an aryl group which is a member of a (or another) photochromic material, such as a naphthopyran or benzopyran, and t is chosen from the integer 1, 2, 3, 4, 5 or 6.

Alternatively, the R$^g$ and R$^h$ groups can each be independently selected from —CH(R$^{10}$)G, where the R$^{10}$ group is chosen from hydrogen, C$_1$-C$_6$ alkyl or an unsubstituted, Mono- or di-substituted aryl group, such as phenyl or naphthyl, and G is chosen, from —CH$_2$OR$^{11}$, where R$^{11}$ is chosen from hydrogen, —C(O)R$^{10}$, C$_1$-C$_6$ alkyl, C$_1$-C$_3$ alkoxy(C$_1$-C$_6$)alkyl, phenyl(C$_1$-C$_3$)alkyl, mono(C$_1$-C$_6$)alkoxy substituted phenyl(C$_1$-C$_3$)alkyl, or an unsubstituted, mono- or di-substituted aryl group, such as phenyl or naphthyl, each of the aryl group substituents (e.g., of the phenyl and naphthyl, group substituents) being independently chosen from C$_1$-C$_6$ alkyl or C$_1$-C$_6$ alkoxy.

Further alternatively, with some embodiments: of the present invention, R$^g$ and R$^h$ together form a spiro substituent selected from a substituted or unsubstituted spiro-carbocyclic ring containing 3 to 6 carbon atoms, a substituted or unsubstituted spiro-heterocyclic ring containing 1 or 2 oxygen atoms and 3 to 6 carbon atoms including the spirocarbon atom, said spiro-carbocyclic ring and spiro-heterocyclic ring being annellated with 0, 1 or 2 benzene rings. The substituents of the recited classes of spiro substituents can be selected from, for example, hydrogen or C$_1$-C$_{20}$ alkyl.

With some embodiments of the present invention, R$^1$ for each m, and R$^2$ for each n, are in each case independently selected from unsubstituted phenyl, substituted phenyl, C$_1$-C$_6$ alkyl, C$_3$-C$_7$ cycloalkyl, C$_1$-C$_8$ haloalkyl, fluoro, chloro, and —O—R$_{10}$'. With further embodiments of the present invention, R$^3$ is selected from hydrogen, C$_1$-C$_8$ alkyl, C$_1$-C$_8$ haloalkyl, and C$_3$-C$_7$ cycloalkyl.

The B and B' groups of the indeno-fused naphthopyran represented by Formula XI, and/or the propargyl alcohol represented by Formula XII can each independently be selected from unsubstituted aryl, substituted aryl, unsubstituted heteroaryl, substituted heteroaryl, polyalkoxy, and polyalkoxy having a polymerizable group. Alternatively, B and B' taken together can form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring.

More particularly, B and B' can each independently be selected from: an aryl group that: is mono-substituted with a reactive substituent or a compatiblizing substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is the reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl.

The phenyl, aryl and heteroaromatic substituents (i.e., the substituents of the substituted phenyl, aryl and heteroaromatic groups) of the B and B' groups may each be independently selected from: hydroxyl, a group —C(=O)R$_{21}$, wherein R$_{21}$ is OR$_{22}$, —N(R$_{23}$)R$_{24}$, piperidino, or morpholino, wherein R$_{22}$ is allyl, C$_1$-C$_6$ alkyl, phenyl, mono(C$_1$-C$_6$)alkyl substituted phenyl, mono(C$_1$-C$_6$)alkoxy substituted phenyl, phenyl(C$_1$-C$_3$)alkyl, mono(C$_1$-C$_6$)alkyl substituted phenyl(C$_1$-C$_3$)alkyl, mono(C$_1$-C$_6$)alkoxy substituted phenyl (C$_1$-C$_3$)alkyl, C$_1$-C$_6$ alkoxy(C$_2$-C$_4$)alkyl or C$_1$-C$_6$ haloalkyl, R$_{23}$ and R$_{24}$ are each independently C$_1$-C$_6$ alkyl, C$_5$-C$_7$ cycloalkyl, phenyl or substituted phenyl, the phenyl substituents being C$_1$-C$_6$ alkyl or C$_1$-C$_6$ alkoxy, and said halo substituent is chloro or fluoro, aryl, mono(C$_1$-C$_{12}$)alkoxyaryl, di(C$_1$-C$_{12}$)alkoxyaryl, mono(C$_1$-C$_{12}$)alkylaryl, di(C$_1$-C$_{12}$) alkylaryl, haloaryl, C$_3$-C$_7$ cycloalkylaryl, C$_3$-C$_7$ cycloalkyl, C$_3$-C$_7$ cycloalkyloxy, C$_3$-C$_7$ cycloalkyloxy(C$_1$-C$_{12}$)alkyl, C$_3$-C$_7$ cycloalkyloxy(C$_1$-C$_{12}$)alkoxy, aryl(C$_1$-C$_{12}$)alkyl, aryl (C$_1$-C$_{12}$)alkoxy, aryloxy, aryloxy(C$_1$-C$_{12}$)alkyl, aryloxy(C$_1$-C$_{12}$)alkoxy, mono- or di(C$_1$-C$_{12}$)alkylaryl(C$_1$-C$_{12}$)alkyl, mono- or di-(C$_1$-C$_{12}$)alkoxyaryl(C$_1$-C$_{12}$)alkyl, mono- or di-(C$_1$-C$_{12}$)alkylaryl(C$_1$-C$_{12}$)alkoxy, mono- or di-(C$_1$-C$_{12}$) alkoxyaryl(C$_1$-C$_{12}$)alkoxy, amino, mono- or di-(C$_1$-C$_{12}$) alkylamino, diarylamino, piperazino, N—(C$_1$-C$_{12}$) alkylpiperazino, N-arylpiperazino, aziridino, indolino, piperidino, morpholino, thiomorpholino, tetrahydroquinolino, tetrahydroisoquinolino, pyrrolidyl, alkyl, $C_1$-$C_{12}$ haloalkyl, $C_1$-$C_{12}$ alkoxy, mono($C_1$-$C_{12}$)alkoxy($C_1$-$C_{12}$)alkyl, acryloxy, methacryloxy, or halogen.

The B and B' groups can also each independently be an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl. The substituents of these mono-substituted groups are each independently selected from $C_1$-$C_{12}$ alkyl, $C_1$-$C_{12}$ alkoxy, phenyl, or halogen.

In addition, the B and B' groups may each be independently selected from a group represented by the following general formulas XIVA or XIVB,

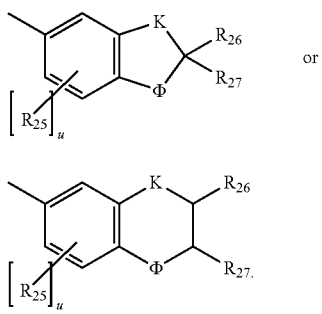

Independently with each of general formulas XIVA and XIVB, K is —$CH_2$— or —O—, and Φ is —O— or substituted nitrogen, provided that when Φ is substituted nitrogen, K is —$CH_2$—. The substituted nitrogen substituents are hydrogen, $C_1$-$C_{12}$ alkyl, or $C_1$-$C_{12}$ acyl. Each $R_{25}$ is independently selected for each occurrence from $C_1$-$C_{12}$ alkyl, $C_1$-$C_{12}$ alkoxy, hydroxy, and halogen, and each u is independently an integer ranging from 0 to 2. The $R_{26}$ and $R_{27}$ groups are each independently hydrogen or $C_1$-$C_{12}$ alkyl.

Each B and B' group can independently be a group represented by the following general formula XV,

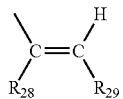

XV

With the group represented by general formula XV, $R_{28}$ is hydrogen or $C_1$-$C_{12}$ alkyl, and $R_{29}$ is an unsubstituted, mono- or di-substituted group chosen from naphthyl, phenyl, furanyl, and thienyl. The substituents of the mono- or di-substituted naphthyls, phenyls, furanyls, and thienyls, are in each case independently selected from $C_1$-$C_{12}$ alkyl, $C_1$-$C_{12}$ alkoxy, or halogen.

The B and B' groups can together form a member selected from, a fluoren-9-ylidene, a mono-substituted fluoren-9-ylidene, or a di-substituted fluoren-9-ylidene. The substituents of the mono-substituted fluoren-9-ylidene, and the di-substituted fluoren-9-ylidene can in each case be independently selected from $C_1$-$C_{12}$ alkyl, $C_1$-$C_{12}$ alkoxy, or halogen.

With some embodiments of the present invention, B and B' are each independently selected from aryl substituted with $C_1$-$C_6$ alkoxy, and aryl (e.g., phenyl) substituted with morpholino.

With some embodiments of the present invention, B and B' can each be independently selected from polyalkoxy, and polyalkoxy having a polymerizable group. The polyalkoxy, and polyalkoxy having a polymerizable group from which B and B' can each be independently selected can be represented by the following Formulas XXV and XXVI.

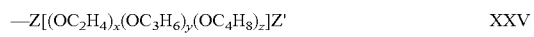

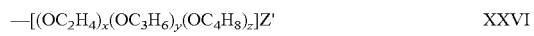

With Formulas XXV and XXVI, —Z is chosen from —C(O)— or —$CH_2$—, Z' is chosen from $C_1$-$C_3$ alkoxy or a polymerizable group. As used herein and in the claims, the term "polymerizable group" means any functional group capable of participating in a polymerization reaction.

With some embodiments, polymerization of the polymerizable indeno-fused naphthopyrans can occur by mechanisms described with regard to the definition of "polymerization" in *Hawley's Condensed Chemical Dictionary*, Thirteenth Edition, 1997, John Wiley & Sons, pages 901-902. Those mechanisms include: by "addition," in which free radicals are the initiating agents that react with the ethylenically unsaturated double bond of the monomer by adding to it on one side at the same time producing a new free electron on the other side; by "condensation," involving the splitting out of a component, such as water molecules, by two reacting monomers; and by so-called "oxidative coupling."

Examples of polymerizable groups include, but are not limited to, hydroxy, thiol, isocyanate groups, oxirane groups (e.g., oxiranylmethyl), radically polymerizable ethylenically unsaturated groups, allyl groups, (meth)acryloxy, and 2-(methacryloxy)ethylcarbamyl. When there are 2 or more polymerizable groups on the naphthopyran, they may be the same or different.

With some embodiments and with further reference to Formulas XXV and XXVI: the group, —($OC_2H_4$)$_x$—, can represent poly(ethylene oxide); the group —($OC_3H_6$)$_y$—, can represent poly(propylene oxide); and the group —($OC_4H_8$)$_z$—, can represent poly(butylene oxide). When used in combination, the poly(ethylene oxide), poly(propylene oxide) and poly(butylene oxide) groups of Formulas XXV and XXVI can be in a random or block order within the polyalkoxy moiety. The subscript letters x, y and z of Formulas XXV and XXVI are each independently a number between 0 and 50, and the sum of x, y and z is between 2 and 50. The sum of x, y and z can be any number that falls within the range of 2 to 50 (e.g., 2, 3, 4 . . . 50). This sum can also range from any lower number to any higher number within the range of 2 to 50 (e.g., 6 to 50, 31 to 50). The numbers for x, y, and z are average values and can be partial numbers (e.g., 9.5).

As previously discussed, each of the $R^1$, $R^2$, $R^3$, B and B' groups can independently be selected from or include at least one of a reactive substituent and/or a compatiblizing substituent. If the various compounds and/or intermediates described previously herein, such as the indeno-fused naphthol represented by Formula I, and/or the indeno-fused naphthopyran represented by Formula XI, include multiple reactive substituents and/or multiple compatiblizing substituents, each reactive substituent and each compatiblizing substituent can be independently chosen.

The reactive substituent and the compatibilizing substituent can each independently be represented in each case by one of:

| | | |
|---|---|---|
| -A'-D-E-G-J (XVI); | -G-E-G-J (XIX); | -D-E-G-J (XXII); |
| -A'-D-J (XVII); | -D-G-J (XX); | -D-J (XXIII); |
| -A'-G-J (XVIII); | -G-J (XXI); and | -A'-J (XXIV). |

With formulas (XVI) through (XXIV), non-limiting examples of groups that -A'- can represent according to various non-limiting embodiments disclosed herein include —O—, —C(=O)—, —CH$_2$—, —OC(=O)— and —NHC(=O)—, provided that if -A'- represents —O—, -A'- forms at least one bond with -J.

Non-limiting examples of groups that -D- can represent according to various non-limiting embodiments include a diamine residue or a derivative thereof, wherein a first amino nitrogen of said diamine residue can form a bond with -A'-, or a substituent or an available position on the compound (such as the indeno-fused naphthol or indeno-fused naphthopyran), and a second amino nitrogen of said diamine residue can form a bond with -E-, -G- or -J; and an amino alcohol residue or a derivative thereof, wherein an amino nitrogen of the amino alcohol residue can form a bond with -A'-, or a substituent or an available position on the compound (such as the indeno-fused naphthol or indeno-fused naphthopyran), and an alcohol oxygen of said amino alcohol residue can form a bond with -E-, -G- or -J. Alternatively, according to various non-limiting embodiments disclosed herein the amino nitrogen of said amino alcohol residue can form a bond with -E-, -G- or -J, and said alcohol oxygen of said amino alcohol residue may form a bond with -A'-, or a substituent or an available position on the compound (such as the indeno-fused naphthol or indeno-fused naphthopyran).

Non-limiting examples of suitable diamine residues that -D- can represent include an aliphatic diamine residue, a cyclo aliphatic diamine residue, a diazacycloalkane residue, an azacyclo aliphatic amine residue, a diazacrown ether residue, and an aromatic diamine residue. Specific non-limiting examples diamine residues that can be used in conjunction with various non-limiting embodiments disclosed herein include the following:

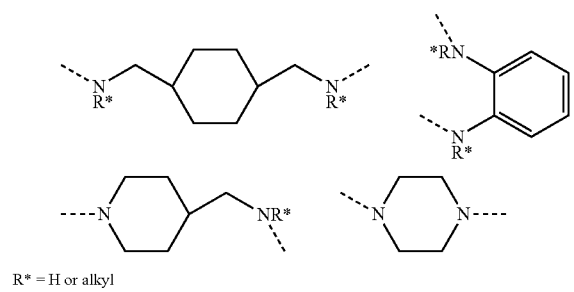

R* = H or alkyl

Non-limiting examples of suitable amino alcohol residues that -D- may represent include an aliphatic amino alcohol residue, a cyclo aliphatic amino alcohol residue, an azacyclo aliphatic alcohol residue, a diazacyclo aliphatic alcohol residue and an aromatic amino alcohol residue. Specific non-limiting examples amino alcohol residues that may be used in conjunction with various non-limiting embodiments disclosed herein include the following:

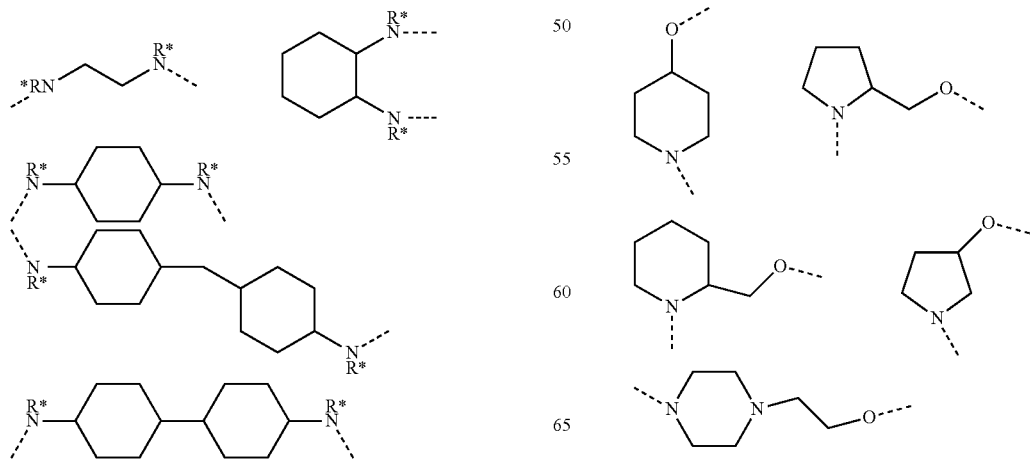

-continued

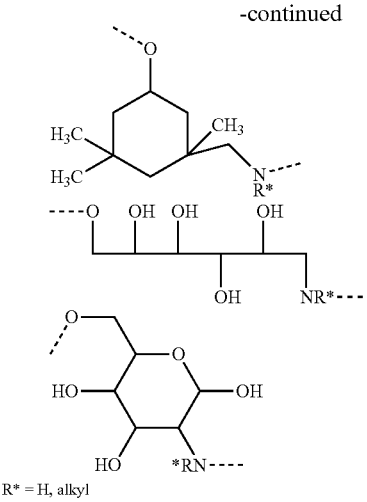

R* = H, alkyl

With continued reference to formulas (XVI) through (XXIV) above, according to various non-limiting embodiments disclosed herein, -E- can represent a dicarboxylic acid residue or a derivative thereof, wherein a first carbonyl group of said dicarboxylic acid residue may form a bond with -G- or -D-, and a second carbonyl group of said dicarboxylic acid residue may form a bond with -G-. Non-limiting examples of suitable dicarboxylic acid residues that -E- can represent include an aliphatic dicarboxylic acid residue, a cycloaliphatic dicarboxylic acid residue and an aromatic dicarboxylic acid residue. Specific non-limiting examples of dicarboxylic acid residues that can be used in conjunction with various non-limiting embodiments disclosed herein include the following:

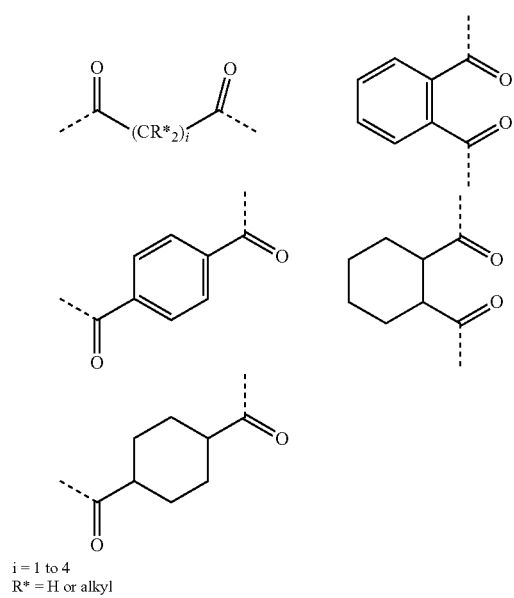

i = 1 to 4
R* = H or alkyl

According to various non-limiting embodiments disclosed herein, -G- can represent a group —[$(OC_2H_4)_x(OC_3H_6)_y(OC_4H_8)_z$]—O—, wherein x, y and z are each independently chosen and range from 0 to 50, and a sum of x, y, and z ranges from 1 to 50; a polyol residue or a derivative thereof, wherein a first polyol oxygen of said polyol residue may form a bond with -A'-, -D-, -E-, or a substituent or an available position on the indeno-fused naphthopyran, and a second polyol oxygen of said polyol may form a bond with -E- or -J; or a combination thereof, wherein the first polyol oxygen of the polyol residue forms a bond with a group —[$(OC_2H_4)_x(OC_3H_6)_y(OC_4H_8)_z$]— to form the group —[$(OC_2H_4)_x(OC_3H_6)_y(OC_4H_8)_z$]—O—), and the second polyol oxygen forms a bond with -E- or -J. Non-limiting examples of suitable polyol residues that -G- can represent include an aliphatic polyol residue, a cyclo aliphatic polyol residue and an aromatic polyol residue.

More particular, illustrative and non-limiting examples of polyols from which the polyol residues that -G- can represent can be formed according to various non-limiting embodiments disclosed herein include: (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

With further reference to formulas (XVI) through (XXIV), according to various non-limiting embodiments disclosed herein, -J can represent a group —K, wherein —K represents a group such as, but not limited to, —$CH_2COOH$, —$CH(CH_3)COOH$, —$C(O)(CH_2)_wCOOH$, —$C_6H_4SO_3H$, —$C_5H_{10}SO_3H$, —$C_4H_8SO_3H$, —$C_3H_6SO_3H$, —$C_2H_4SO_3H$ and —$SO_3H$, wherein "w" ranges from 1 to 18. According to other non-limiting embodiments -J can represent hydrogen that forms a bond with an oxygen or a nitrogen of linking group to form a reactive moiety such as —OH or —NH. For example, according to various non-limiting embodiments disclosed herein, -J can represent hydrogen, provided that if -J represents hydrogen, -J is bonded to an oxygen of -D- or -G-, or a nitrogen of -D-.

According to still further non-limiting embodiments, -J can represent a group -L or residue thereof, wherein -L can represent a reactive moiety. For example, according to various non-limiting embodiments disclosed herein -L can represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

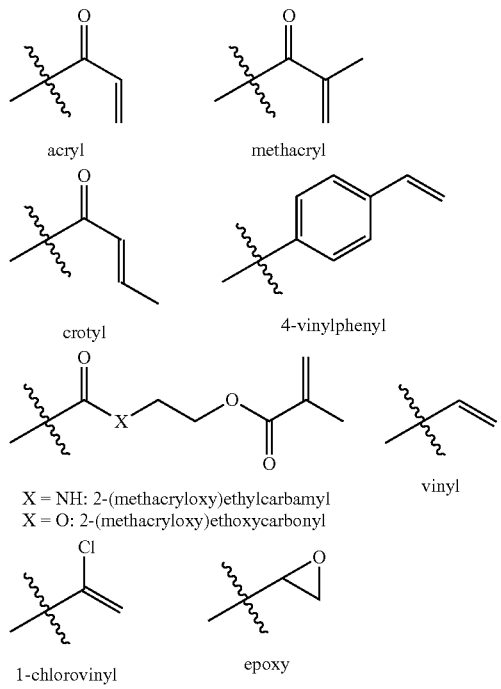

As previously discussed, -G- can represent a residue of a polyol, which is defined herein to include hydroxy-containing carbohydrates, such as those set forth in U.S. Pat. No. 6,555,028 at col. 7, line 56 to col. 8, line 17, which disclosure is hereby specifically incorporated by reference herein. The polyol residue can be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol can be represented by q-$(OH)_a$ and the residue of the polyol can be represented by the formula —O-q-$(OH)_{a-1}$, wherein q is the backbone or main chain of the polyhydroxy compound and "a" is at least 2.

Further, as discussed above, one or more of the polyol oxygens of -G- can form a bond with -J (i.e., forming the group -G-J). For example, although not limiting herein, wherein the reactive and/or compatiblizing substituent comprises the group -G-J, if -G- represents a polyol residue and -J represents a group —K that contains a carboxyl terminating group, -G-J can be produced by reacting one or more polyol hydroxyl groups to form the group —K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group —K that contains a sulfo or sulfono terminating group, although not limiting herein, -G-J can be produced by acidic condensation of one or more of the polyol hydroxyl groups with $HOC_6H_4SO_3H$; $HOC_5H_{10}SO_3H$; $HOC_4H_8SO_3H$; $HOC_3H_6SO_3H$; $HOC_2H_4SO_3H$; or $H_2SO_4$, respectively. Further, although not limiting herein, if -G- represents a polyol residue and -J represents a group -L chosen from acryl, methacryl, 2-(methacryloxy)ethylcarbamyl and epoxy, -L can be added by condensation of the polyol residue with acryloyl chloride, methacryloyl chloride, 2-isocyanatoethyl methacrylate or epichlorohydrin, respectively.

The indeno-fused naphthopyrans prepared by the method of the present invention, can be used to render compositions and/or articles photochromic. Examples of articles that can be rendered photochromic by the indeno-fused naphthopyrans of the present invention include, but are not limited to, optical elements, displays, windows (or transparencies), mirrors, and components or elements of liquid crystal cells. As used herein the term "optical" means pertaining to or associated with light and/or vision. Examples of optical elements that can be rendered photochromic include, without limitation, ophthalmic elements, display elements, windows, mirrors, and liquid crystal cell elements. As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, magnifying lenses, protective lenses, visors, goggles, as well as, lenses for optical instruments (for example, cameras and telescopes). As used herein the term "display" means the visible or machine-readable representation of information in words, numbers, symbols, designs or drawings. Non-limiting examples of display elements include screens, monitors, and security elements, such as security marks. As used herein the term "window" means an aperture adapted to permit the transmission of radiation there-through. Non-limiting examples of windows include automotive and aircraft transparencies, windshields, filters, shutters, and optical switches. As used herein the term "mirror" means a surface that specularly reflects a large fraction of incident light. As used herein the term "liquid crystal cell" refers to a structure containing a liquid crystal material that is capable of being ordered. One non-limiting example of a liquid crystal cell element is a liquid crystal display.

Articles can be rendered photochromic with the indeno-fused naphthopyrans of the present invention by methods including, but not limited to, imbibition methods, cast-in-place methods, coating methods, in-mold coating methods, over-mold methods, and lamination methods. With imbibition methods, the indeno-fused naphthopyran is typically diffused into a polymeric material of a previously formed or fabricated article, such as a substrate or previously applied coating or film. Imbibition can be performed by immersing the polymeric material of a previously formed or fabricated article in a solution containing the indeno-fused naphthopyran, with or without heating. Thereafter, although not required, the indeno-fused naphthopyran can be bonded with the polymeric material (e.g., of the substrate or coating).

With cast-in-place methods, the indeno-fused naphthopyran can be mixed with: a polymer and/or oligomer composition in solution or melt form; or monomer composition in liquid form, so as to form a castable photochromic composition. The castable photochromic composition is then typically introduced into the cavity of a mold (e.g., a lens mold). The castable photochromic composition is then set (e.g., cured) within the mold so as to form a photochromic article.

With articles that include a substrate, the indeno-fused naphthopyrans of the present invention can be connected to at least a portion of the substrate as part of a coating that is connected to at least a portion of the substrate. The substrate can be a polymeric substrate or an inorganic substrate (such as, but not limited to, a glass substrate). The indeno-fused naphthopyran of the present invention can be incorporated into at least a portion of a coating composition prior to application of the coating composition to the substrate. Alternatively, a coating composition can be applied to the substrate, at least partially set, and thereafter the indeno-fused naphthopyran of the present invention can be imbibed into at least a portion of the coating. As used herein, the terms "set" and "setting" include, without limitation, curing, polymerizing, cross-linking, cooling, and drying.

Photochromic articles can be prepared using the indeno-fused naphthopyrans of the present invention by art-recognized in-mold coating (or in-mold casting) methods. With in-mold coating methods, a photochromic coating composition including the indeno-naphthopyran of the present invention, which can be a liquid coating composition or a powder coating composition, is applied to at least a portion of the interior surface of a mold, and then at least partially set. Thereafter, a polymer solution or melt, or oligomeric or monomeric solution or mixture is cast or molded within the mold cavity and in contact with the previously applied photochromic coating composition, and at least partially set. The resulting photochromic article is then removed from the mold. Non-limiting examples of powder coatings in which the indeno-naphthopyrans according to various non-limiting embodiments disclosed herein can be employed are set forth in U.S. Pat. No. 6,068,797 at col. 7, line 50 to col. 19, line 42, which disclosure is hereby specifically incorporated by reference herein.

Photochromic articles prepared using the indeno-fused naphthopyrans of the present invention can also be formed by art-recognized over-mold methods. Over-mold methods typically involve forming a substrate within a mold, and then forming an interior space between the substrate and an interior surface of the mold, into which a photochromic coating composition is then subsequently introduced (e.g., injected) and then set (e.g., cured). Alternatively, over-mold methods can involve introducing a previously formed substrate into a mold, such that an interior space is defined between the substrate and an interior mold surface, and thereafter a photochromic coating composition is introduced (e.g., injected) into the interior space.

Photochromic articles prepared using the indeno-fused naphthopyrans of the present invention can also be formed by art-recognized lamination methods. With lamination methods, a film comprising the indeno-fused naphthopyrans of the present invention can be adhered or otherwise connect to a portion of the substrate, with or without an adhesive and/or the application of heat and pressure. Thereafter, if desired, a second substrate can be applied over the first substrate and the two substrates can be laminated together (e.g., by the application of heat and pressure) to form an element wherein the film comprising the indeno-fused naphthopyran is interposed between the two substrates. Methods of forming films comprising a photochromic material can include for example and without limitation, combining a photochromic material with a polymeric solution or oligomeric solution or mixture, casting or extruding a film therefrom, and, if required, at least partially setting the film. Additionally or alternatively, a film can be formed (with or without a photochromic material) and imbibed with the photochromic material.

The indeno-fused naphthopyrans prepared by the method of the present invention, can be used alone or in combination with other photochromic materials. Classes of photochromic materials that can be used in combination (e.g., in mixture) with the indeno-fused naphthopyrans of the present invention include, but are not limited to: spiro(indoline)naphthoxazines and spiro(indoline)benzoxazines, for example as described in U.S. Pat. Nos. 3,562,172, 3,578,602, 4,215,010, 4,342,668, 5,405,958, 4,637,698, 4,931,219, 4,816,584, 4,880,667, and 4,818,096; benzopyrans, for example as described in U.S. Pat. Nos. 3,567,605, 4,826,977, 5,066,818, 4,826,977, 5,066,818, 5,466,398, 5,384,077, 5,238,931, and 5,274,132; photochromic organo-metal dithizonates, such as, (arylazo)-thioformic arylhydrazidates, e.g., mercury dithizonates which are described in, for example, U.S. Pat. No. 3,361,706; and fulgides and fulgimides, e.g., the 3-furyl and 3-thienyl fulgides and fulgimides which are described in U.S. Pat. No. 4,931,220 at column 20, line 5 through column 21, line 38.

The present invention is more particularly described in the following examples, which are intended to be illustrative only, since numerous modifications and variations therein will be apparent to those skilled in the art. Unless otherwise specified, all parts and all percentages are by weight.

EXAMPLES

In Part 1 of the Examples, the synthesis procedures used to make the naphthols of Examples 1-3, and the photochromic materials of Examples 1A and 3A is described. Part 2 describes the photochromic performance testing and results for photochromic compounds of Examples 1A and 3A.

Part 1: Synthesis of the Naphthols of Examples 1-3 and Photochromic Compounds of Examples 1A and 3A Example 1

Step 1

Solid maleic anhydride (110 g) was dissolved in cumene (400 mL) in a 1 L single-neck flask, followed by addition of $^t$butyl peroxide (11 mL). The resulting mixture was heated under refluxing condition for 20 hours. The solvent was removed under reduced pressure. The product was obtained as viscous brown oil (260 g). The recovered product containing 2-(2-phenylpropan-2-yl)succinic acid was used for next step without further purification.

Step 2

The product from Step 1 (260 g) was dissolved in xylene (500 mL) in a 1 L single-neck flask equipped with a Dean-Star Trap and water condenser, followed by addition of dodecyl benzene sulfonic acid (18 g). The resulting mixture was heated under refluxing condition for 4 hours. The solvent was removed under reduced pressure. The product was obtained as viscous brown oil (280 g). The product containing 3-(2-phenylpropan-2-yl)dihydrofuran-2,5-dione was used in the next step without purification.

Step 3

The product from Step 2, (280 g), was dissolved in dichloromethane (1.4 L) in a 2 L three-neck flask. The resulting mixture was cooled to 0-10° C. with brine-ice mixture. Anhydrous aluminum chloride (330 g) was added to the mixture slowly through a solid addition funnel. Hydrochloric gas generated from the reaction was absorbed by an aqueous potassium hydroxide solution. The cooling batch was removed 1 hour after the addition. After another hour the reaction was quenched by pouring into icy water (2 L) and acidified with hydrochloric acid (12N, 800 mL). The product was extracted with ethyl acetate (2×1 L). The emulsion was disrupted by the addition of brine (1 L). The organic layers were recovered, combined, dried over anhydrous sodium sulfate and concentrated under reduced pressure to provide product (360 g). The recovered product was purified by silica gel chromatography using a mixture of ethyl acetate/hexanes as eluent to provide the desired product (150 g). NMR showed the product to have a structure consistent with 2-(1,1-dimethyl-3-oxo-2,3-dihydro-1H-inden-2-yl)acetic acid Step 4

The product (10 g) from Step 3 and 2-amino-2-methylpropanol (5 g) were dissolved in xylene (45 mL) in a 250 mL one-neck round bottom (RB) flask with a Dean-Stark trap and water condenser under a $N_2$ blanket. The resulting mixture was heated under refluxing condition for 20 hours. The mixture was then was cooled and purified by silica gel chromatography using a mixture of ethyl acetate/hexanes as eluent to provide one major oily product (6 g). NMR showed the product to have a structure consistent with 2-((4,4-dimethyl-4,5-dihydrooxazol-2-yl)methyl)-3,3-dimethyl-2,3-dihydro-1H-inden-1-one.

Step 5

The oily product from Step 4 was dissolved in anhydrous tetrahydrofuran (40 mL) in a 250 mL one-neck round bottom flask under $N_2$ blank. Magnesium bromide (4 g) was added to the same flask. The flask was seated in ice water bath. 3-Methoxyphenyl magnesium bromide in tetrahydrofuran solution (40 mL, 1M) was added to the mixture through an additional funnel over 10 minutes. The ice water bath was removed upon the addition. The resulting mixture was stirred for 1 hour and then poured into ice water. The slurry was acidified by 10% hydrochloric acid solution and extracted with diethyl ether. The top layer was condensed to provide an oily residue. The residue was dissolved in a mixture of dioxane and 3N hydrochloric acid solution (50/50 mL) and the resulting mixture was heated under refluxing conditions for 3 hours. The mixture was cooled and extracted with ethyl acetate. The recovered top layer was dried over sodium sulfate and concentrated to provide an oily residue. The residue was purified by silica gel chromatography using a mixture of ethyl acetate/hexanes as eluent to provide an oily product (6 g) containing 2-(3-(2-methoxyphenyl)-1,1-dimethyl-1H-inden-2-yl)acetic acid that was used in the next step without further purification.

Step 6

The product from Step 5 (6 g) was dissolved in acetic anhydride (30 mL) in a 250 mL one-neck round bottom flask under $N_2$ blank. The resulting solution was heated under refluxing for 1.5 hour. Bismuth(III) trifluoromethanesulfonate (0.1 g) catalyst was added to the hot mixture. Refluxing was continued for 2 hours. The reaction mixture was cooled and the pH was reduced 6-7 with potassium hydroxide and sodium bicarbonate. The product was extracted with ethyl acetate and the solution was dried over sodium sulfate. The solvent was stripped off under reduced pressure. The resulting product containing 2-methoxy-7,7-dimethyl-7H-benzo[c]fluoren-5-yl acetate was dried under vacuum to provide product (6 g) that was used in next step without purification.

Step 7

The product from Step 6 (6 g) was dissolved in anhydrous methanol (50 mL) in a 250 mL one-neck round bottom flask under $N_2$ blank. Concentrated hydrochloric acid (1 mL) was added to the flask. The resulting solution was heated under refluxing for 2 hours. The reaction mixture was condensed and the residue was purified by silica gel chromatography using a mixture of ethyl acetate/hexanes as eluent to provide the desired product (1.4 g). NMR analysis showed the product to have a structure consistent with 2-methoxy-7,7-dimethyl-7H-benzo[c]fluoren-5-ol as shown in the following graphic formula:

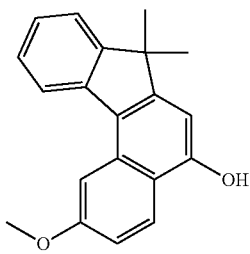 [SMILES: COc1ccc2c(O)cc3c(c2c1)-c1ccccc1C3(C)C]

Example 1A

The product from Example 1 (1.5 g), was dissolved in dichloromethane (20 mL) in a single-necked 100 mL flask, followed by addition of dodecyl benzene sulfonic acid (0.02 g). 1,1-Bis(4-methoxyphenyl)-2-propyn-1-ol (0.7 g) was added to the reaction mixture. The mixture was stirred at room temperature and monitored by TLC analysis. Upon completion of the reaction, the product was purified by silica gel chromatography using a mixture of ethyl acetate/hexanes as eluent. The major product was then recrystallized to provide the desired product (1 g). NMR showed the product to have a structure consistent with 3,3-bis(4-methoxyphenyl)-7-methoxy-13,13-dimethyl-3H,13H-indeno[2',3':3,4]naphtho[1,2-b]pyran as represented by the following graphic formula.

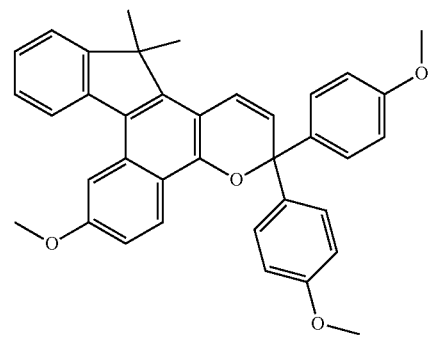 [SMILES: COc1ccc(C2(c3ccc(OC)cc3)C=Cc3c4c(c5cc(OC)ccc5c3O2)-c2ccccc2C4(C)C)cc1]

Example 2

Step 1

4-Methoxyphenyl magnesium bromide in tetrahydrofuran (200 mL, 1M) was charged to a 1 L one-neck round bottom flask through an additional funnel under $N_2$ blank. The product from Step 3 of Example 1, 2-(1,1-dimethyl-3-oxo-2,3-dihydro-1H-inden-2-yl)acetic acid (9 g) in anhydrous tetrahydrofuran (60 mL) solution was added dropwise to the Grignard solution over 30 minutes. The reaction mixture was stirred at room temperature for 20 hours. The mixture was poured into ice water and the resulting slurry was acidified by the addition of 10% hydrochloric acid (200 mL). The mixture was extracted with ethyl acetate. The recovered top layer was concentrated to provide the major product (24 g). The recovered product and pyridinium p-toluenesulfonate (1 g) were dissolved in toluene (150 mL) in a 500 mL one-neck round bottom flask with a Dean-Stark trap and water condenser. The mixture was heated under refluxing condition for 3 hours. The reaction mixture was condensed to provide the major product (24 g). The residue was filtered through a silica gel column using a mixture of ethyl acetate/hexanes as eluent to afford the major product (13 g). The recovered product containing 24343-methoxyphenyl)-1,1-dimethyl-1H-inden-2-yl)acetic acid was used in next step without further purification.

Step 2

The product from Step 1 (20 g) was dissolved in acetic anhydride (50 mL) in a 500 mL one-neck round bottom flask equipped with water condenser under $N_2$ blank. Bismuth(III) trifluoromethanesulfonate (0.1 g) catalyst was added to the mixture. The mixture was heated under refluxing condition for 6 hours. The mixture was concentrated and the recovered product containing 3-methoxy-7,7-dimethyl-7H-benzo[c]fluoren-5-yl acetate was used in next step without further purification.

Step 3

The procedure of Step 7 of Example 1 was followed except that the product from Step 2 above was used in place of 3-methoxy-7,7-dimethyl-7H-benzo[c]fluoren-5-yl acetate to produce the desired product. Mass Spectroscopy showed the product to have a molecular weight of 290 which was consistent with the structure of 3-methoxy-7,7-dimethyl-7H-benzo[c]fluoren-5-ol shown in the following graphic formula:

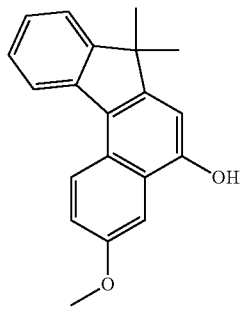 [SMILES: COc1ccc2c3c(cc(O)c2c1)C(C)(C)c1ccccc1-3]

Example 3

Step 1

A 3,5-difluorophenylmagnesium bromide in diethyl ether solution (0.8M, 350 mL) was charged to a 2 L two-neck round bottom flask under $N_2$ blank. The product from Step 3 of Example 1, 2-(1,1-dimethyl-3-oxo-2,3-dihydro-1H-inden-2-yl)acetic acid (8 g) in anhydrous tetrahydrofuran (60 mL) solution was added dropwise to the Grignard solution over 30 minutes. The reaction mixture was stirred at room temperature for 20 hours. The mixture was poured into ice water and the resulting slurry was acidified with 10% hydrochloric acid solution (300 mL). The mixture was extracted with ethyl acetate. The recovered top layer was concentrated to provide product (24 g). The product and pyridinium p-toluenesulfonate (1 g) were dissolved in toluene (100 mL) in a 500 mL one-neck round bottom flask with a Dean-Stark trap and water condenser. The mixture was heated under refluxing condition for 3 hours. The reaction mixture was then concentrated to provide major product (20 g). The recovered product containing 2-(3-(2,4-difluorophenyl)-1,1-dimethyl-1H-inden-2-yl)acetic acid was used in next step without further purification.

Step 2

The product from Step 1 (20 g) was dissolved in acetic anhydride (50 mL) in a 500 mL one-neck round bottom flask equipped with water condenser under $N_2$ blank. Bismuth(III) trifluoromethanesulfonate (0.1 g) catalyst was added to the mixture. The mixture was heated under refluxing condition for 6 hours. The resulting mixture was condensed and the recovered oily product containing 2,4-difluoro-7,7-dimethyl-7H-benzo[c]fluoren-5-yl acetate was used in next step without further purification.

Step 3

The product from Step 2 (20 g), was dissolved in methanol (100 mL) in a single-neck 250 mL round bottom flask, followed by addition of concentrated hydrochloric acid (37%, 0.5 mL). The mixture was heated under refluxing condition for 3 hours. The solvent was removed under reduced pressure to provide the major product (18 g). The major product was purified by silica gel chromatography to yield the desired product (10 g). UV Spectroscopy showed the product to have spectral profile consistent with the structure of 2,4-difluoro-7,7-dimethyl-7H-benzo[c]fluoren-5-ol shown in the following graphic formula:

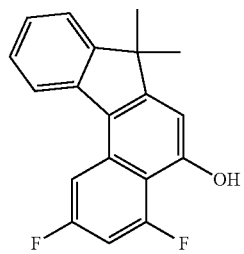 [SMILES: CC1(C)c2ccccc2-c2c1cc(O)c1c(F)cc(F)cc21]

Example 3A

The procedure of Example 1A was followed except that the product of Example 3 was used in place of the product of Example 1 and p-toluenesulfonic acid monohydrate (0.1 g) was used in place of dodecyl benzene sulfonic acid (1 drop). NMR showed the product to have a structure consistent with 3,3-bis(4-methoxyphenyl)-5,7-difluoro-13,13-dimethyl-3H, 13H-indeno[2',3':3,4]naphtho[1,2-b]pyran as represented by the following graphic formula:

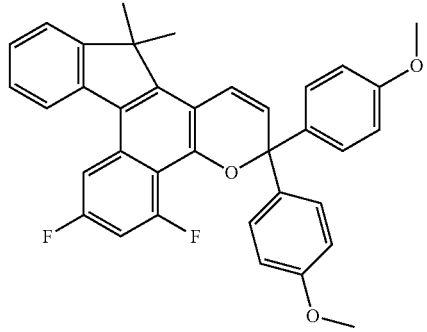 [SMILES: COc1ccc(C2(c3ccc(OC)cc3)C=Cc3c4c(c5cc(F)cc(F)c5c3O2)-c2ccccc2C4(C)C)cc1]

Part 2: Photochromic Performance Testing and Results

The photochromic performance of the photochromic materials of Examples 1A and 3A were tested as follows. A quantity of the photochromic material to be tested, calculated to yield a $1.5 \times 10^{-3}$M solution, was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'- azobis(2-methyl propionitrile) (AIBN). The photochromic material was dissolved into the monomer blend by stirring and gentle heating if necessary. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours and then lower it to 60° C. for over a 2 hour interval. After the mold was opened, the polymer sheet was cut using a utility knife to score the surface and snap into 2 inch (5.1 cm) test squares.

The photochromic test squares prepared as described above were tested for photochromic response on an optical bench. Prior to testing on the optical bench, the photochromic test squares were exposed to 365 nm ultraviolet light for about 15 minutes to cause the photochromic material to transform from the ground state-form to an activated-state form, and then placed in a 75° C. oven for about 15 minutes to allow the photochromic material to revert back to the ground state-form. The test squares were then cooled to room temperature, exposed to fluorescent room lighting for at least 2 hours, and then kept covered (that is, in a dark environment) for at least 2 hours prior to testing on an optical bench maintained at 73° F. (23° C.).

The optical bench fitted with a Schott 3 mm KG-2 bandpass filter, neutral density filter(s) and a Newport Model #67005 300-watt Xenon arc lamp with Model #69911 power supply in association with a Newport Model 689456 Digital Exposure/Tinier was used to control the intensity of the irradiance beam utilized for activation of the sample. A Uniblitz model #CS25S3ZM0 with model#VMM-D3 controller) high-speed computer controlled shutter, a fused silica condensing lens for beam collimation of this activation lamp beam though a quartz glass water bath sample chamber.

A custom made broadband light source for monitoring response measurements was directed through the sample such that the angle between the activation source and the monitoring beam is 30 degrees with the sample positioned perpendicular to this monitoring beam. This broad beam light source is obtained by collecting and combining separately filtered light from a 100-Watt tungsten halogen lamp (controlled by a Lambda UP60-14 constant voltage powder supply) with a split-end, bifurcated fiber optical cable to enhance the short wavelength light intensity. After passing through the sample, this monitoring light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

The $\lambda_{max\text{-}vis}$ is the wavelength in the visible spectrum at which the maximum absorption of the activated-state form of the photochromic compound in a test square occurs. The $\lambda_{max\text{-}vis}$ wavelength was determined by testing the photochromic test squares in a Varian Cary 4000 UV-Visible spectrophotometer.

The change in Optical density at saturation for each test sample was determined by opening the shutter from the xenon lamp and measuring the transmittance after exposing the test chip to 3 W/m² UVA radiation for 30 minutes. The change in Optical density at saturation was calculated using the formula: $\Delta OD = \log(\%\,Tb/\%\,Ta)$, where % Tb is the percent transmittance in the bleached state, % Ta is the percent transmittance in the activated state both at the $\lambda_{max\text{-}vis}$ and the logarithm is to the base 10. The first fade half life ("$T_{1/2}$") or bleach rate is the time interval in seconds for the absorbance of the activated-state form of the photochromic material in the test squares to reach one half the ΔOD at saturation value at room temperature (23° C.), after removal of the source of activating light. The Sensitivity (ΔOD/Min) is a measure of how quickly the sample darkens and is calculated from the equation $\Delta OD_{sen} = \Delta OD_{5\,min} \times 12$. The results are listed in Table 1.

TABLE 1

Photochromic Performance Test Results

| Example # | $\lambda_{max\text{-}vis}$ (nm) | Sensitivity (ΔOD/Min) | ΔOD at saturation | T ½ (sec) |
|---|---|---|---|---|
| 1A | 546 | 0.56 | 1.16 | 217 |
| 3A | 551 | 0.55 | 0.64 | 73 |

The present invention has been described with reference to specific details of particular embodiments thereof. It is not intended that such details be regarded as limitations upon the scope of the invention except insofar as and to the extent that they are included in the accompanying claims.

We claim:
1. A method of making an indeno-fused naphthopyran represented by the following Formula XI,

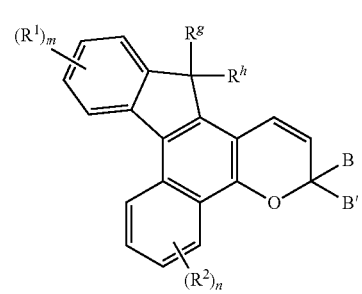

XI wherein, m and n are each independently selected from 0 to 4, $R^1$ for each m is halogen or $R_{10'}$, wherein $R_{10'}$ is hydrogen, $R^2$ for each n is independently hydrocarbyl optionally interrupted with at least one of —O—, or —S—, and combinations thereof; substituted hydrocarbyl interrupted with at least one of —O—, or —S—, and combinations thereof; halogen; —O—$R_{10}$', wherein each $R_{10}$' is independently selected from hydrogen, hydrocarbyl or substituted hydrocarbyl, $R^g$ and $R^h$ are each independently hydrogen or hydrocarbyl, and B and B' are each independently selected from unsubstituted aryl, substituted aryl, unsubstituted heteroaryl, substituted heteroaryl, B and B' taken together form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring, said method comprising, (a) reacting an alkyl benzene represented by Formula II with maleic anhydride in the presence of a bishydrocarbyl peroxide represented by the formula $R^a$—O—O—$R^b$, where $R^a$ and $R^b$ are each independently hydrocarbyl or substituted hydrocarbyl, thereby forming a succinic acid substituted intermediate represented by Formula III,

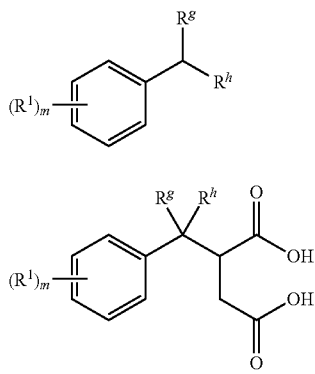

II

III (b) converting the succinic acid substituted intermediate represented by Formula III to a succinic anhydride substituted intermediate represented by Formula IV,

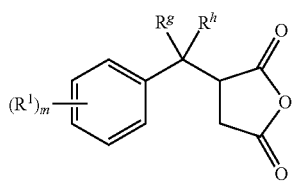

IV (c) converting the succinic anhydride substituted intermediate represented by Formula IV to an indanone acid intermediate represented by Formula V,

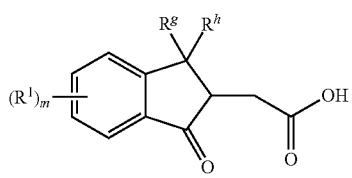

V (d) reacting the indanone acid intermediate represented by Formula V with a nucleophile represented by Formula VI to form a substituted indanone intermediate represented by at least one of Formula VIIa, Formula VIIb and Formula VIIc,

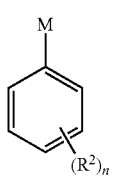

VI wherein M represents a counterion comprising a metal selected from Mg, Li, Cu and combinations thereof,

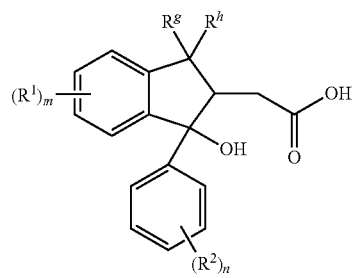

VIIa

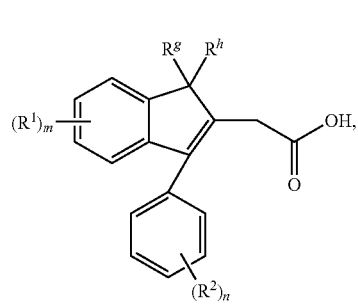

VIIb

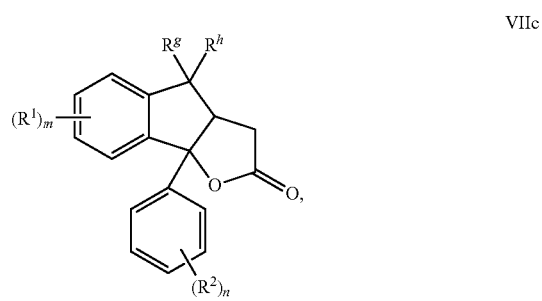

VIIc (e) converting said substituted indanone intermediate represented by at least one of Formula VIIa, Formula VIIb and Formula VIIc to an indeno-fused naphthol represented by Formula I,

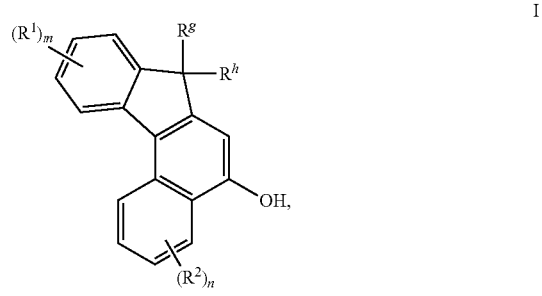

I and (f) reacting the indeno-fused naphthol represented by Formula I with a propargyl alcohol represented by Formula XII thereby forming said indeno-fused naphthopyran represented by Formula XI,

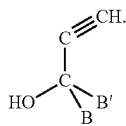

XII

2. The method of claim 1, wherein reacting said alkyl benzene represented by Formula II with maleic anhydride, is performed in the presence of a free radical generator comprising a bishydrocarbyl peroxide represented by the formula $R^a$—O—O—$R^b$, where $R^a$ and $R^b$ are each independently linear or branched $C_1$ to $C_{10}$ alkyl.

3. The method of claim 1, wherein conversion of the said succinic anhydride substituted intermediate represented by Formula IV to said indanone acid intermediate represented by Formula V, is performed in the presence of a Lewis acid.

4. The method of claim 3, wherein said Lewis acid is $AlCl_3$.

5. The method of claim 1, wherein conversion of said indanone intermediate represented by at least one of Formula VIIa, Formula VIIb and Formula VIIc to said indeno-fused naphthol represented by Formula I, is conducted in the presence of a material selected from carboxylic acid halide, carboxylic acid anhydride, sulfonyl halide and combinations thereof, thereby forming an indeno-fused naphtho-intermediate represented by the following Formula X,

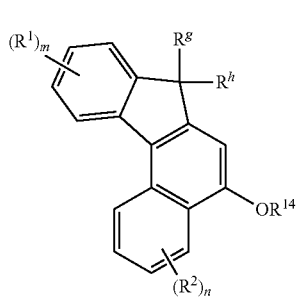

X wherein $R^{14}$ is selected from —C(O)—$R^{15}$ and —S(O)(O) $R^{15}$, wherein $R^{15}$ is selected from hydrocarbyl and halohydrocarbyl, and reacting said indeno-fused naphtho-intermediate represented by Formula X with a Brønsted acid, thereby forming said indeno-fused naphthol represented by Formula I.

6. The method of claim 1, wherein conversion of said indanone intermediate represented by at least one of Formula VIIa, Formula VIIb and Formula VIIc to said indeno-fused naphthol represented by Formula I, is conducted in the presence of a Brønsted acid.

7. The method of claim 6, wherein said Brønsted acid is selected from carboxylic acids, sulfonic acids, phosphoric acids, and combinations thereof.

8. The method of claim 1, wherein
$R^2$ for each n is independently
halogen selected from fluoro and chloro;
$C_1$-$C_6$ alkyl;
$C_3$-$C_7$ cycloalkyl;
substituted or unsubstituted phenyl, the phenyl substituents being selected from halogen, halo($C_1$-$C_6$)alkyl, $C_1$-$C_6$ alkyl or $C_1$-$C_6$ alkoxy;
—O—$R_{10}'$, wherein $R_{10}'$ is $C_1$-$C_6$ alkyl, phenyl($C_1$-$C_3$) alkyl, mono($C_1$-$C_6$)alkyl substituted phenyl($C_1$-$C_3$) alkyl, mono($C_1$-$C_6$)alkoxy substituted phenyl($C_1$-$C_3$) alkyl, ($C_1$-$C_6$)alkoxy($C_2$-$C_4$)alkyl, $C_3$-$C_7$ cycloalkyl, or mono($C_1$-$C_4$)alkyl substituted $C_3$-$C_7$ cycloalkyl;
or
two adjacent $R^2$ groups, independently together form a group represented by one of XIIID and XIIIE:

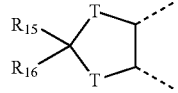

XIIID

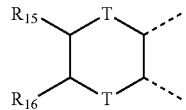

XIIIE wherein T and T' are each oxygen, where $R_{15}$ and $R_{16}$ are as set forth above;

B and B' are each independently:
an aryl group that is mono-substituted with a reactive substituent or a compatiblizing substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is the reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein each of the phenyl, aryl and heteroaromatic substituents are each independently:

hydroxyl, a group —C(=O)$R_{21}$, where $R_{21}$ is —O$R_{22}$, —N($R_{23}$)$R_{24}$, piperidino, or morpholino, wherein $R_{22}$ is allyl, $C_1$-$C_6$ alkyl, phenyl, mono($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl, $R_{23}$ and $R_{24}$ are each independently $C_1$-$C_6$ alkyl, $C_5$-$C_7$ cycloalkyl, phenyl or substituted phenyl, the phenyl substituents being $C_1$-$C_6$ alkyl or $C_1$-$C_6$ alkoxy, and said halo substituent is chloro or fluoro, aryl, mono($C_1$-$C_{12}$)alkoxyaryl, di($C_1$-$C_{12}$)alkoxyaryl, mono($C_1$-$C_{12}$)alkylaryl, di($C_1$-$C_{12}$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_{12}$)alkyl, $C_3$-$C_7$ cycloalkyloxy ($C_1$-$C_{12}$)alkoxy, aryl($C_1$-$C_{12}$)alkyl, aryl($C_1$-$C_{12}$) alkoxy, aryloxy, aryloxy($C_1$-$C_{12}$)alkyl, aryloxy($C_1$-$C_{12}$)alkoxy, mono- or di($C_1$-$C_{12}$)alkylaryl($C_1$-$C_{12}$) alkyl, mono- or di-($C_1$-$C_{12}$)alkoxyaryl($C_1$-$C_{12}$)alkyl, mono- or di-($C_1$-$C_{12}$)alkylaryl($C_1$-$C_{12}$)alkoxy, mono- or di-($C_1$-$C_{12}$)alkoxyaryl($C_1$-$C_{12}$)alkoxy, amino, mono- or di-($C_1$-$C_{12}$)alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{12}$ alkyl, $C_1$-$C_{12}$ haloalkyl, $C_1$-$C_{12}$ alkoxy, mono($C_1$-$C_{12}$)alkoxy($C_1$-$C_{12}$)alkyl, acryloxy, methacryloxy, or halogen;

an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{12}$ alkyl, $C_1$-$C_{12}$ alkoxy, phenyl, or halogen;

a group represented by one of:

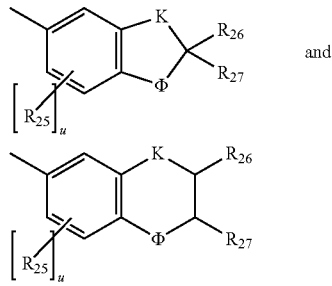

wherein K is —$CH_2$— or —O—, and Φ is —O— or substituted nitrogen, provided that when Φ is substituted nitrogen, K is —$CH_2$—, the substituted nitrogen substituents being hydrogen, $C_1$-$C_{12}$ alkyl, or $C_1$-$C_{12}$ acyl, each $R_{25}$ being independently chosen for each occurrence from $C_1$-$C_2$ alkyl, $C_1$-$C_{12}$ alkoxy, hydroxy, and halogen, $R_{26}$ and $R_{27}$ each being independently hydrogen or $C_1$-$C_{12}$ alkyl, and u is an integer ranging from 0 to 2; or a group represented by:

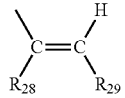

wherein $R_{28}$ is hydrogen or $C_1$-$C_{12}$ alkyl, and $R_{29}$ is an unsubstituted, mono-, or di-substituted group chosen from naphthyl, phenyl, furanyl, and thienyl, wherein the substituents are $C_1$-$C_{12}$ alkyl, $C_1$-$C_{12}$ alkoxy, or halogen; or B and B' taken together form one of a fluoren-9-ylidene, mono-, or di-substituted fluoren-9-ylidene, each of said fluoren-9-ylidene substituents being independently chosen from $C_1$-$C_{12}$ alkyl, $C_1$-$C_{12}$ alkoxy, and halogen.

9. The method of claim 8, wherein, $R^2$ for each n are independently selected from unsubstituted phenyl, substituted phenyl, $C_1$-$C_6$ alkyl, $C_3$-$C_7$ cycloalkyl, $C_1$-$C_8$ haloalkyl, fluoro, chloro, and —O—$R_{10}{'}$, and B and B' are each independently selected from aryl substituted with $C_1$-$C_6$ alkoxy, and aryl substituted with morpholino.

* * * * *